(12) United States Patent
Favero et al.

(10) Patent No.: US 10,759,746 B2
(45) Date of Patent: Sep. 1, 2020

(54) HYDRATED CRYSTALLINE FORM OF 2-ACRYLAMIDO-2-METHYLPROPANE SULFONIC ACID

(71) Applicant: S.P.C.M. SA, Andrezieux Boutheon (FR)

(72) Inventors: Cédrick Favero, Andrezieux Boutheon (FR); Johann Kieffer, Andrezieux Boutheon (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 0 days.

(21) Appl. No.: 16/496,031

(22) PCT Filed: Mar. 19, 2018

(86) PCT No.: PCT/FR2018/050652
§ 371 (c)(1),
(2) Date: Sep. 20, 2019

(87) PCT Pub. No.: WO2018/172676
PCT Pub. Date: Sep. 27, 2018

(65) Prior Publication Data
US 2020/0031765 A1    Jan. 30, 2020

(30) Foreign Application Priority Data
Mar. 20, 2017 (FR) .................... 17 52288

(51) Int. Cl.
| | | |
|---|---|---|
| C07C 309/15 | (2006.01) |
| C08F 20/58 | (2006.01) |
| C09K 8/68 | (2006.01) |
| C09K 8/80 | (2006.01) |
| E21B 43/26 | (2006.01) |
| C09K 8/588 | (2006.01) |
| E21B 43/16 | (2006.01) |
| C02F 11/147 | (2019.01) |
| C02F 1/56 | (2006.01) |
| C02F 103/10 | (2006.01) |

(52) U.S. Cl.
CPC .............. *C07C 309/15* (2013.01); *C02F 1/56* (2013.01); *C02F 11/147* (2019.01); *C08F 20/58* (2013.01); *C09K 8/588* (2013.01); *C09K 8/68* (2013.01); *C09K 8/80* (2013.01); *E21B 43/16* (2013.01); *E21B 43/26* (2013.01); *C02F 2103/10* (2013.01); *C07B 2200/13* (2013.01); *C09K 2208/28* (2013.01)

(58) Field of Classification Search
CPC ............................. C07C 309/15; C08F 20/58
See application file for complete search history.

(56) References Cited

U.S. PATENT DOCUMENTS

| | | | | |
|---|---|---|---|---|
| 4,219,498 A | * | 8/1980 | Doi ........................ | C07C 303/42 562/105 |
| 6,448,347 B1 | | 9/2002 | Quinn et al. | |
| 2010/0274048 A1 | | 10/2010 | Wakayama | |

FOREIGN PATENT DOCUMENTS

| | | |
|---|---|---|
| CN | 102351744 A | 2/2012 |
| JP | H05125037 A | 5/1993 |
| JP | 2003137857 A | 5/2003 |
| JP | 3412158 B2 | 6/2003 |
| JP | 2009155324 A | 7/2009 |
| WO | 2009072480 A1 | 6/2009 |

OTHER PUBLICATIONS

International Search Report (and English translation) and Written Opinion of the International Searching Authority for International Application No. PCT/FR2018/050652 dated Jun. 4, 2018.

* cited by examiner

*Primary Examiner* — Karen Cheng
(74) *Attorney, Agent, or Firm* — Heslin Rothenberg Farley & Mesiti P.C.

(57) ABSTRACT

The present invention relates to a hydrated crystalline form of 2-acrylamido-2-methylpropane sulfonic acid having a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° degrees (+/−0.1°).
The present invention also relates to a production method for this form of 2-acrylamido-2-methylpropane sulfonic acid and a preparation method for an aqueous solution A of a salt of this form of 2-acrylamido-2-methylpropane sulfonic acid, and the (co)polymer of this form of -acrylamido-2-methylpropane sulfonic acid.

6 Claims, 12 Drawing Sheets

HYDRATED CRYSTALLINE FORM OF 2-ACRYLAMIDO-2-METHYLPROPANE SULFONIC ACID

CROSS REFERENCE TO RELATED APPLICATIONS

This application is a national stage filing under section 371 of International Application No. PCT/FR2018/050652 filed on Mar. 19, 2018, and published on Sep. 27, 2018 as WO 2018/172676, which claims priority to French Application No. 1752288, filed on Mar. 20, 2017. The entire contents of WO 2018/172676 are hereby incorporated herein by reference.

FIELD OF THE INVENTION

The field of the invention relates to a crystalline form of 2-acrylamido-2-methylpropane sulfonic acid (ATBS). More specifically, the present invention relates to a hydrated crystalline form of 2-acrylamido-2-methylpropane sulfonic acid. The invention also relates to the method of producing the hydrated crystalline form of 2-acrylamido-2-methylpropane sulfonic acid.

DESCRIPTION OF THE PRIOR ART

2-Acrylamido-2-methylpropane sulfonic acid, also known as ATBS, is widely used as an additive in acrylic fibers, and as a raw material for producing polymers used as dispersant, flocculant thickener or superabsorbant in diverse sectors such as the oil industry, construction, textiles, water treatment (desalination of sea water, mineral industry, etc.) and cosmetics.

The reaction used in the 2-acrylamido-2-methylpropane sulfonic acid preparation method is as in the reaction scheme below, in which acrylonitrile is present in excess so as to be both the reaction solvent and a reagent. Acrylonitrile is put in contact with fuming sulfuric acid (oleum) and isobutylene.

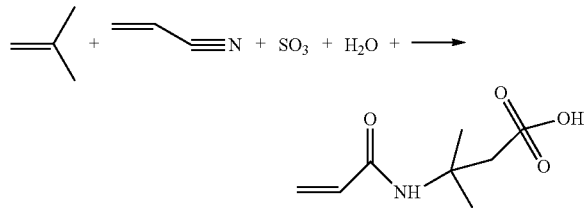

A by-product that can be generated during this synthesis is acrylamide.

2-Acrylamido-2-methylpropane sulfonic acid is not soluble in the solvent acrylonitrile. Consequently the product of the reaction is in a form of a crystal suspension in the reaction solvent.

As examples, documents U.S. Pat. No. 6,448,347 and CN 102351744 describe a method of producing 2-acrylamido-2-methylpropane sulfonic acid continuously. 2-Acrylamido-2-methylpropane sulfonic acid is then separated from the acrylonitrile, generally by filtration, then dried.

Drying the 2-acrylamido-2-methylpropane sulfonic acid is necessary to reduce the remaining quantity of acrylonitrile and acrylamide present in the crystal. These two compounds are classed as carcinogenic, mutagenic or reprotoxic (CMR). It is therefore necessary to proceed with effective filtration to remove as much of the acrylonitrile as possible, and then to dry 2-acrylamido-2-methylpropane sulfonic acid to obtain low acrylonitrile and acrylamide contents.

It is known to the person skilled in the art that 2-acrylamido-2-methylpropane sulfonic acid crystals have a crystallographic arrangement that produces a needle-shaped solid.

Needle-shaped crystals are known to the person skilled in the art to present macroscopic properties that pose difficulties in solid handling and transport operations (poor solid flowability, clumping, low resistance to a shear force), processing operations (poor filterability, difficulty in drying, attrition).

For 2-acrylamido-2-methylpropane sulfonic acid, the extra problems that are met are generally low crystal particle size for needle-shaped crystals, the density of the solid, and the explosive nature of the fine dust.

These macroscopic properties are directly related to the morphology of the crystals and to their specific surface area. For a needle-shaped crystal, the specific surface area is high.

Patents WO 2009/072480, JP 2008/307822 and JP 2003/137857 describe that the 2-acrylamido-2-methylpropane sulfonic acid crystals obtained are needle-shaped.

SUMMARY OF THE INVENTION

The present invention relates to a specific form of 2-acrylamido-2-methylpropane sulfonic acid denoted below as "hydrated crystalline form of 2-acrylamido-2-methylpropane sulfonic acid."

Another feature of the invention is the method of producing the hydrated crystalline form of 2-acrylamido-2-methylpropane sulfonic acid.

The invention also relates to an aqueous solution of a 2-acrylamido-2-methylpropane sulfonic acid salt prepared from the hydrated crystalline form of 2-acrylamido-2-methylpropane sulfonic acid.

The invention also relates to the use of the hydrated crystalline form of 2-acrylamido-2-methylpropane sulfonic acid for producing water-soluble, water-swelling or superabsorbent (co)polymers.

Another feature of the invention relates to the use of (co)polymers made from the hydrated crystalline form of 2-acrylamido-2-methylpropane sulfonic acid, and more precisely in the field of enhanced oil and gas recovery.

DESCRIPTION OF THE INVENTION

The present invention relates to a hydrated crystalline form of 2-acrylamido-2-methylpropane sulfonic acid having a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° degrees. The uncertainty in these peaks is generally of the order of 0.1°.

X-ray crystallography, radiocrystallography or X-ray diffractometry is an analytical technique for studying the structure of the crystalline material on the atomic scale. It uses the physical phenomenon of X-ray diffraction. A diffractometer having a copper source may be used.

A powder formed from a given crystalline phase will always produce diffraction peaks in the same directions. So this diffraction diagram forms a real signature of the crystalline phase. It is therefore possible to determine the nature of each crystalline phase within a mixture or a pure product.

This signature is specific to each organic or inorganic compound, and presents in the form of a list of peaks with positions at the 2θ angle (2-theta).

This technique is used to characterize the material, particularly the different crystalline forms that may exist for a given chemical molecule.

The invention also relates to a hydrated crystalline form of 2-acrylamido-2-methylpropane sulfonic acid having a Fourier transform infrared spectrum comprising peaks at 3280 cm$^{-1}$, 3126 cm$^{-1}$, 1657 cm$^{-1}$, 1595 cm$^{-1}$, 1453 cm$^{-1}$, 1395 cm$^{-1}$, 1307 cm$^{-1}$, 1205 cm$^{-1}$, 1164 cm$^{-1}$, 1113 cm$^{-1}$, 1041 cm$^{-1}$, 968 cm$^{-1}$, 885 cm$^{-1}$, 815 cm$^{-1}$, 794 cm'. The uncertainty in these peaks is generally of the order of 8 cm'. Advantageously, this is the solid spectrum obtained conventionally in a salt such as KBr.

Fourier transform infrared spectroscopy is the analysis of vibrations emitted, absorbed or diffused by the molecules. This technique is sensitive to close interactions (influence of the lattice unit on the bonds). In the majority of cases, the Fourier transform infrared spectra for different crystalline systems differ significantly. So the Fourier transform infrared spectrum reflects details about the crystalline structure of an organic compound.

Generally, and unless otherwise indicated, the X-ray diffraction diagram and the infrared spectrum are obtained at 20° C. and atmospheric pressure of 1 atmosphere (101,325 Pa).

The invention also relates to a hydrated crystalline form of 2-acrylamido-2-methylpropane sulfonic acid having minimum ignition energy greater than 400 mJ, preferably greater than 500 mJ.

The minimum ignition energy represents the minimum energy that must be provided to a compound to cause ignition. The energy may be electric or thermal. The minimum ignition energy is an essential piece of data for taking into account the risk of explosion during product handling (transfer, storage, reaction, shaping, etc.).

The minimum ignition energy depends on the powder's properties (composition) and its macromolecular structure (particle size, crystalline form, specific surface area).

For solids, this energy is the minimum energy of an electrical spark that can ignite a cloud of dust. The higher the minimum ignition energy, the lower the risk the solid presents during use, handling, storage.

Minimum ignition energy was measured according to standard NF EN 13821.

The present invention also relates to a hydrated crystalline form of 2-acrylamido-2-methylpropane sulfonic acid presenting 4 thermal phenomena with the differential scanning calorimetry technique, at 70° C., 100° C., 150° C. and 190° C. The relative uncertainty when observing these phenomena is generally of the order of 10° C., advantageously 5° C. or less.

The thermal phenomena are measured by differential scanning calorimetry (DSC). This technique measures the heat variation associated with thermal denaturation of the compound when it is heated at a constant rate, for example with a heating ramp of 10° C./minute.

It is generally recognized that the thermal phenomenon that occurs at 190° C. (+/−10° C.) is related to the melting point of 2-acrylamido-2-methylpropane sulfonic acid.

In an advantageous manner, the hydrated crystalline form of 2-acrylamido-2-methylpropane sulfonic acid according to the invention has a water/2-acrylamido-2-methylpropane sulfonic acid molar ratio of 1.

The invention also relates to the method of producing the hydrated crystalline form of 2-acrylamido-2-methylpropane sulfonic acid comprising at least the following successive steps:
1) Mix 2-acrylamido-2-methylpropane sulfonic acid with an aqueous solution, advantageously for at least 1 minute, to form suspension A,
2) Heat suspension A, advantageously to a temperature of between 40 and 150° C., to produce a solution B of 2-acrylamido-2-methylpropane sulfonic acid,
3) Cool solution B, advantageously to a temperature of between −40 and 100° C., advantageously for a period of between 1 and 1200 minutes, to produce a suspension C of crystals,
4) Solid/liquid separation from suspension C and isolate crystals from suspension C obtained from step 3) in the form of a composition 1 in which the crystals advantageously represent between 40 and 99% by weight of composition 1. The crystals obtained are in the hydrated crystalline form.

The temperature of steps 2) and 3) may vary depending in particular on the 2-acrylamido-2-methylpropane sulfonic acid concentration. The person skilled in the art will know how to adapt the temperature variation to optimize crystal formation.

Step 1):

2-Acrylamido-2-methylpropane sulfonic acid comes from a production method as described previously (acrylonitrile, fuming sulfuric acid and isobutylene). 2-Acrylamido-2-methylpropane sulfonic acid may be in the form of fine powder or shaped in a controlled manner by a method such as compaction, granulation, or extrusion.

The ratio by weight of aqueous solution mixed with 2-acrylamido-2-methylpropane sulfonic acid is advantageously between 0.1:1 and 5:1, more preferably between 0.2:1 and 3:1.

According to a specific embodiment, the aqueous solution may comprise up to 20% by weight of organic solvent 1, preferably from 1 to 15% by weight of organic solvent 1, more preferably from 2 to 10% by weight of organic solvent 1.

According to another specific embodiment of the invention, the aqueous solution comprises at least 80% by weight of water and up to 20% by weight of organic solvent 1, preferably between 85% and 99% by weight of water and from 1% to 15% by weight of organic solvent 1, more preferably between 90% and 98% by weight of water and from 2% to 10% by weight of organic solvent 1.

Organic solvent 1 is advantageously chosen from the following compounds:
organic acids, advantageously carboxylic acids comprising from 1 to 8 carbons,
amides comprising advantageously from 1 to 8 carbon atoms,
alcohols comprising advantageously from 1 to 8 carbon atoms,
ketones comprising advantageously from 1 to 8 carbon atoms,
ethers comprising advantageously from 1 to 8 carbon atoms,
esters comprising advantageously from 1 to 8 carbon atoms,
alkanes comprising advantageously from 1 to 8 carbon atoms,
halogenated hydrocarbon compounds comprising advantageously from 1 to 8 carbon atoms, nitriles comprising advantageously from 1 to 8 carbon atoms, or their mixtures.

These compounds may be linear or branched. They may be may be saturated or comprise unsaturations, for example C≡N in the case of nitriles.

Preferably, solvent 1 is chosen from acrylonitrile, isopropanol, acetic acid or their mixtures. Preferably, solvent 1 is acrylonitrile.

Solvent 1 is generally in liquid form at the temperature at which steps 2) and 3) are conducted. In addition, it is advantageously miscible with water.

Solvent 1 may, if need be, solubilize any impurities or by-products present with 2-acrylamido-2-methylpropane sulfonic acid used to form suspension A. By contrast, 2-acrylamido-2-methylpropane sulfonic acid is not necessarily soluble in solvent 1.

According to another specific embodiment of the invention, the aqueous solution may comprise at least 80% by weight of water and up to 20% by weight of inorganic acid, preferably between 80% and 99% by weight of water and from 1% to 20% by weight of inorganic acid, more preferably between 85% and 98% by weight of water and 2% to 15% by weight of inorganic acid.

Preferably, the inorganic acid is sulfuric acid. In this case, the aqueous solution of sulfuric acid may be prepared by diluting an acid containing less than 80% of water, or of a source of $SO_3$ such as oleum or sulfur trioxide.

So the aqueous solution may comprise at least one organic solvent 1 and/or at least one inorganic acid other than 2-acrylamido-2-methylpropane sulfonic acid.

The mixing time between the aqueous solution and 2-acrylamido-2-methylpropane sulfonic acid is advantageously at least 1 minute. During mixing, the aqueous solution may be added sequentially before or after 2-acrylamido-2-methylpropane sulfonic acid. During mixing, the aqueous solution and the 2-acrylamido-2-methylpropane sulfonic acid may be added simultaneously.

The mixing temperature is generally below 40° C. The lower temperature limit is limited by the melting temperature of the aqueous solution or of suspension A.

The products of step 1) may be mixed using diverse technologies. As examples and in a non-limiting manner, we can cite reactors with stirrers, loop reactors, static mixers, microreactors, plug-flow reactors, stirred filter-dryer reactors, for example Nutsche, paddle blenders, double-cone blenders, plow blenders, and disk blenders.

Step 2):

Suspension A obtained in step 1) is heated to a temperature of between 40 and 150° C., more preferably between 50 and 120° C. to produce a solution B.

The time for solution B to reach the temperature does not influence the benefits of the invention.

Diverse technologies may be used to achieve the temperature rise of suspension A to produce a solution B. As examples and in a non-limiting manner, we can cite reactors with stirrers, loop reactors, static mixers, microreactors, plug-flow reactors, stirred filter-dryer reactors, for example Nutsche, heat exchangers, paddle blenders, double-cone blenders, plow blenders, disk blenders, falling-film evaporators, wiped-film evaporators, and reboilers.

Step 2) solubilizes 2-acrylamido-2-methylpropane sulfonic acid.

In a specific embodiment of the invention, solution B may undergo a solid/liquid separation operation to remove all insoluble particles.

Step 3:

Solution B obtained in step 2) is cooled to a temperature of between −40 and 100° C., more preferably between −20 and 50° C. As already indicated, the person skilled in the art will know how to adjust the temperature depending on the 2-acrylamido-2-methylpropane sulfonic acid concentration and/or depending on the melting point of solvent 1 and/or the inorganic acid of step 1).

In a general manner, the temperature of step 3) is less than the temperature of step 2).

The cooling time is advantageously between 1 minute and 1200 minutes.

The cooling rate does not have to be constant throughout the process. As an example, solution B may be cooled by 5° C. per hour during the first three hours, and then be cooled at a rate of 10° C. per hour until the final temperature is reached.

During the cooling of solution B, crystals of 2-acrylamido-2-methylpropane sulfonic acid are formed and precipitate, to form a suspension C.

Diverse technologies may be used to achieve the cooling of solution B to produce suspension C. As examples and in a non-limiting manner, we can cite reactors with stirrers, loop reactors, static mixers, microreactors, plug-flow reactors, stirred filter-dryer reactors, for example Nutsche, heat exchangers, paddle blenders, double-cone blenders, plow blenders, disk blenders, falling-film evaporators, wiped-film evaporators, and non-stirred reactors.

In a specific embodiment of the invention, hydrated crystals of 2-acrylamido-2-methylpropanesulfonic acid previously prepared may be added during this step to modify the formation of suspension C. This is crystallization seeding, which can lead to better control of the crystallization temperature, crystal particle size, particle size distribution, final product purity and, optionally, yield.

Step 4:

The crystals of hydrated 2-acrylamido-2-methylpropane sulfonic acid contained in suspension C obtained from step 3) are isolated through a liquid/solid separation step and are presented in the form of a composition 1. As examples and in a non-limiting manner, we can cite the use of a centrifugal filter, a decanter, a filter press, a stirred smoothing filter, a belt filter, a disk filter, or a rotating drum filter. In a preferred manner, the liquid/solid separation is conducted using a centrifugal filter. The liquid/solid separation may also be conducted by gravity decantation.

Step 4) is advantageously carried out at a temperature of between −40 and 100° C., more preferably between −20 and 50° C.

Preferably after step 4) of liquid/solid separation, the crystals of 2-acrylamido-2-methylpropane sulfonic acid are not dried.

Isolated composition 1 has a 2-acrylamido-2-methylpropane sulfonic acid crystal content advantageously of between 40 and 99%, more preferably between 60 and 99% by weight, even more preferably between 60 and 98% by weight. The remainder of composition 1 comprises principally water.

After step 4), the 2-acrylamido-2-methylpropane sulfonic acid crystals are characterized as being crystals of 2-acrylamido-2-methylpropane sulfonic acid in hydrated form.

Furthermore, the liquid phase obtained after the liquid/solid separation contains principally water and 2-acrylamido-2-methylpropane sulfonic acid at saturation, and a minor amount of organic solvent 1 and/or the inorganic acid. According to a specific embodiment of the invention, this liquid phase after separation may be used totally or partially in the aqueous solution in step 1).

Step 5):

In an optional step 5), composition 1 containing the crystals obtained from step 4) is washed using a washing solution.

The washing solution is advantageously an aqueous solution that may comprise up to 20% of organic solvent 1.

Preferably, the washing solution comprises at least 80% by weight of water and up to 20% by weight of organic solvent 1, preferably between 80% and 99% by weight of water and from 1% to 20% by weight of organic solvent 1, more preferably between 85% and 98% by weight of water and from 2% to 15% by weight of organic solvent 1.

As already stated, organic solvent 1 is chosen from organic acids, amides, alcohols, ketones, ethers, esters, alkanes, halogenated hydrocarbon compounds, nitriles, or their mixtures. Preferably, solvent 1 is chosen from acrylonitrile, isopropanol, acetic acid or their mixtures. More preferably, solvent 1 is acrylonitrile.

According to a specific embodiment of the invention, the washing of composition 1 obtained from step 4) is conducted by spraying the washing solution on said composition 1.

According to another specific embodiment of the invention, the washing of composition 1 obtained from step 4) is conducted by putting said composition 1 into suspension in the washing solution.

The ratio by weight between the aqueous washing solution and the composition 1 obtained from step 4) is advantageously between 0.05:1 and 10:1 and more preferably between 0.1:1 and 5:1.

This washing step is advantageously conducted at a temperature of between −20 and 100° C. The person skilled in the art will know how to adjust the temperature so as not to solubilize the crystals in hydrated form 2-acrylamido-2-methylpropane sulfonic acid.

According to a specific embodiment, the aqueous washing solution may comprise up to 60% by weight of 2-acrylamido-2-methylpropane sulfonic acid.

The crystals in hydrated form of 2-acrylamido-2-methylpropane sulfonic acid obtained from optional step 5) may be isolated from the washing solution by a liquid/solid separation step, in the form of a composition 2. As examples and in a non-limiting manner, we can cite the use of a vertical or horizontal centrifugal filter, a decanter, a filter press, a belt filter, a disk filter, a pressure filter, or a rotating drum filter. The liquid/solid separation may also be conducted by gravity decantation.

According to a specific embodiment of the invention, the washing solution recovered may be used totally or partially again in step 5), with or without a previous treatment step.

According to a specific embodiment of the invention, the washing solution may be used totally or partially in the aqueous solution in step 1), with or without a previous treatment step.

Step 6):

In an optional step 6), the composition 2 obtained from step 5) is dried. As examples and in a non-limiting manner, we can cite the use of all convection, conduction or radiation drying technologies (fluidized bed dryer, traversed bed dryer, conveyor belt drying, microwave drying on heated stirred smoothing filter, drying by high frequency radiation, infrared, spray drying).

The drying operation may be conducted at atmospheric pressure or under vacuum.

The drying step may be conducted in a batch or continuous manner.

During the production method, i.e. during steps 1) to 6), and regardless of the step, it is possible to add at least one polymerization inhibitor so as to prevent any polymerization of 2-acrylamido-2-methylpropane sulfonic acid. This inhibitor may be chosen in a non-limiting manner from hydroquinone, paramethoxyphenol, phenothiazine, 2,2,6,6-tetramethyl(piperidin-1-yl)oxyl, 4-hydroxy-2,2,6,6-tetramethylpiperidin-1-oxyl, phenylene diamine derivatives, or their mixtures.

Preferably, the inhibitor is paramethoxyphenol or 4-hydroxy-2,2,6,6-tetramethylpiperidin-1-oxyl.

The quantity of inhibitor added relative to the quantity of 2-acrylamido-2-methylpropane sulfonic acid added in step 1) is advantageously between 0.001% and 5% by weight, more preferably between 0.01% and 1% by weight.

The inhibitor may be added during one or more steps of the method. Preferentially, it is added in an additional quantity during step 1). More preferably, the inhibitor forms part of the aqueous solution added in step 1).

The production method (steps 1) to 6)) may be conducted continuously or discontinuously (in batches).

The invention also relates to a preparation method of an aqueous solution A of a 2-acrylamido-2-methylpropane sulfonic acid salt prepared from the hydrated crystalline form.

The preparation method of an aqueous solution A of a 2-acrylamido-2-methylpropane sulfonic acid salt comprises the following steps:

a) Preparing an aqueous solution X of 2-acrylamido-2-methylpropane sulfonic acid having a concentration advantageously between 1 and 700 g/L, b) Putting in contact and mixing the aqueous solution X with a compound Y chosen from an alkali or alkaline earth metal hydroxide, an alkali or alkaline earth metal oxide, ammonia, an amine having the following formula $NR_1R_2R_3$ ($R_1$, $R_2$ and $R_3$ being advantageously hydrocarbon groups, in particular alkyl groups) or an alkali or alkaline earth metal carbonate.

Step a):

The hydrated crystalline form of 2-acrylamido-2-methylpropane sulfonic acid may be in the form of a fine powder or shaped in a controlled manner by a method such as compaction, or granulation, or extrusion.

The aqueous solution X of 2-acrylamido-2-methylpropanesulfonic acid is advantageously prepared by mixing the hydrated crystalline form of 2-acrylamido-2-methylpropane sulfonic acid and an aqueous solution Z.

The mixing time between the aqueous solution Z and 2-acrylamido-2-methylpropane sulfonic acid is advantageously at least 1 minute. During mixing, the aqueous solution Z and the 2-acrylamido-2-methylpropane sulfonic acid may be added simultaneously, without a preferred order, or simultaneously.

The mixing temperature is generally below 60° C. The lower temperature limit is limited by the crystallization temperature of aqueous solution Z or of aqueous solution X of 2-acrylamido-2-methylpropane sulfonic acid.

The aqueous solution Z is composed mainly of water, and may contain 2-acrylamido-2-methylpropane sulfonic acid or its salt prepared previously from any of the bases previously listed (compound Y).

The products of step a) may be mixed using diverse technologies. As examples and in a non-limiting manner, we can cite reactors with stirrers, loop reactors, static mixers, microreactors, plug-flow reactors, stirred filter-dryer reactors, for example Nutsche, paddle blenders, double-cone blenders, plow blenders, and disk blenders.

Step b):

Compound Y may be in solid form or liquid form.

According to a specific embodiment of the invention, compound Y is in solid form, preferably in the form of powder or shaped by a method such as compaction, or granulation, or extrusion.

According to another specific embodiment compound Y is in liquid form, preferably in the form of an aqueous solution Y.

When compound Y is an alkali metal or alkaline earth metal hydroxide, it may be chosen from sodium hydroxide, potassium hydroxide, lithium hydroxide, magnesium hydroxide and calcium hydroxide.

When compound Y is an alkaline earth metal oxide, it may be chosen from calcium oxide and magnesium oxide.

When compound Y is an amine having formula $NR_1R_2R_3$ where $R_1$, $R_2$ and $R_3$ are independently a hydrogen atom or a carbon chain containing from 1 to 22 carbon atoms, advantageously a linear chain, $R_1$, $R_2$ and $R_3$ not being simultaneously a hydrogen atom. In a general manner, ammonia ($NH_3$) is preferred to amines having formula $NR_1R_2R_3$.

In a preferred manner, compound Y is an aqueous solution of an alkali or alkaline earth metal hydroxide. Preferably, the alkali metal hydroxide is sodium hydroxide.

When compound Y is in the form of aqueous solution Y, the compound Y concentration in the solution is advantageously between 0, 1 and 70 mass %.

During the mixing of aqueous solution X with aqueous solution Y, the temperature is advantageously maintained between −10 and 60° C., preferably between 0 and 30° C.

The molar ratio of 2-acrylamido-2-methylpropane sulfonic acid and compound Y is advantageously between 1:0.1 and 1:1.1, more preferably between 1:0.5 and 1:1.05.

During mixing, aqueous solution X may be added sequentially before or after compound Y (or aqueous solution Y). During mixing, aqueous solution X and compound Y (or its aqueous solution) may be added simultaneously.

Preferably, aqueous solution X is added first, followed by compound Y (or its aqueous solution Y).

It is possible, regardless of the step, to add at least one polymerization inhibitor during the preparation method of solution A of the 2-acrylamido-2-methylpropane sulfonic acid salt prepared from the hydrated crystalline solid form. This inhibitor may be chosen in a non-limiting manner from hydroquinone, paramethoxyphenol, phenothiazine, 2,2,6,6-tetramethyl(piperidin-1-yl)oxyl, 4-hydroxy-2,2,6,6-tetramethylpiperidin-1-oxyl, phenylene diamine derivatives, or their mixtures.

Preferably, the inhibitor is paramethoxyphenol.

The invention also relates to the use of the new hydrated crystalline form of 2-acrylamido-2-methylpropane sulfonic acid for producing (co)polymers. This feature of the invention also covers the use of salts of the hydrated crystalline form of 2-acrylamido-2-methylpropane sulfonic acid for producing (co)polymers.

Quite unexpectedly, the Applicant has discovered that the (co)polymer according to the invention has improved properties especially in terms of filterability and improved chemical and thermal stability compared to polymers prepared from conventional ATBS. These properties are particularly useful in enhanced oil or gas recovery techniques from conventional reservoirs, shale or oil sands.

The present invention therefore also relates to a (co) polymer obtained from at least 2-acrylamido-2-methylpropanesulfonic acid, in its acidic and/or salified form, at least a portion of the 2-acrylamido-2 acid methyl propane sulfonic acid being in hydrated crystalline form and having an X-ray powder diffraction pattern comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° degrees 2-theta (+/− 0.1°).

It can be a copolymer (obtained from several different monomers) or a homopolymer.

The monomer 2-acrylamido-2-methylpropanesulfonic acid in its hydrated crystalline form can be in the acid and/or salified form, the salt being advantageously obtained from a compound chosen from an alkali metal or alkaline earth metal hydroxide, an alkali or alkaline earth metal oxide, ammonia, an amine of the following formula $NR_1R_2R_3$ or an alkali metal or alkaline earth metal carbonate.

In general, the salified form of anionic monomers can be obtained before and/or during and/or after their polymerization. It is advantageously obtained before the polymerization, especially in the case of the hydrated crystalline form of 2-acrylamido-2-methylpropanesulfonic acid.

According to a specific embodiment of the invention, the polymer is a homopolymer of the hydrated crystalline form of 2-acrylamido-2-methylpropane sulfonic acid.

According to another specific embodiment of the invention, the (co)polymer is obtained from at least 2-acrylamido-2-methylpropane sulfonic acid, 50% to 100% of which are the hydrated crystalline form, more preferably 70 to 100%, even more preferably 100%.

The (co)polymer according to the invention is advantageously obtained from 1 to 100 mol % of 2-acrylamido-2-methylpropanesulfonic acid, preferably between 2 and 60 mol % of 2-acrylamido-2-methylpropanesulfonic acid, even more preferably between 3 and 25 mol % of 2-acrylamido-2-methylpropanesulfonic acid; 50% to 100% of 2-acrylamido-2-methylpropanesulfonic acid are advantageously in the hydrated crystalline form, more preferably 70 to 100%, and even more preferably 100%.

In general, the skilled person will know, if necessary, how to adjust the amount of optional additional monomers (anionic and/or cationic and/or zwitterionic) listed below to reach 100 mol %.

According to another particular embodiment of the invention, the (co)polymer may be obtained from 2-acrylamido-2-methylpropanesulfonic acid of which 50% to 100% is advantageously in the hydrated crystalline form (more advantageously 70 to 100%, and even more preferably 100%) and from at least one non-ionic monomer and/or at least one anionic monomer and/or at least one cationic monomer and/or a zwitterionic monomer.

According to another particular embodiment of the invention, the polymer is a copolymer of the hydrated crystalline form of 2-acrylamido-2-methylpropanesulfonic acid and at least one non-ionic monomer.

The non-ionic monomer may notably be selected from the group comprising water-soluble vinyl monomers, and particularly acrylamide; N-isopropylacrylamide; N,N-dimethylacrylamide; N-vinylformamide; acryloyl morpholine; N,N-diethyl acrylamide; N-tert-butyl acrylamide; N-tert-octylacrylamide; N-vinylpyrrolidone; N-vinylcaprolactam; N-vinyl-imidazole, hydroxyethyl methacrylamide, hydroxypropylacrylate, isoprenol and diacetone acrylamide. Advantageously, the non-ionic monomer is acrylamide.

According to a particular embodiment, the copolymer is advantageously obtained from 1 to 99 mol % of non-ionic monomer(s), preferably between 40 and 95 mol % and more preferably between 45 and 90 mol %, relative to the total number of monomers. In this case, the copolymer is advantageously obtained from 0.1 to 99 mol % of 2-acrylamido-2-methylpropane sulfonic acid, 50% to 100% being in hydrated crystalline form, more preferably from 70 to 100%, even more preferably 100%.

The anionic monomer(s) may have acrylic, vinyl, maleic, fumaric, malonic, itaconic, allylic functional groups and contain a carboxylate, phosphonate, phosphate, sulfate, sulfonate group or another anionic group. The anionic monomer may be in acid form and/or in the form of an alkaline earth metal salt, an alkali metal salt or an ammonium salt. Examples of suitable monomers comprise acrylic acid, methacrylic acid, itaconic acid, crotonic acid, maleic acid, fumaric acid, acrylamide undecanoic acid, acrylamide 3-methylbutanoic acid, maleic anhydride; monomers of the strong acid type having for example a function of the sulfonic acid or phosphoric acid type, such as vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, 2-acrylamido-2-methypropane disulfonic acid; and salts of these monomers like their alkali metal, alkaline earth metal, or ammonium salts. In this list, the strong acid monomers mentioned having a sulfonic acid function do not include the hydrated crystalline form of 2-acrylamido-2-methylpropane sulfonic acid according to the invention.

According to a particular embodiment, the copolymer is advantageously obtained from 1 to 99 mol % of anionic monomer(s), preferably between 2 and 60 mol % and more preferably between 3 and 25 mol %, relative to the total number of monomers. These percentages include the monomer of the hydrated crystalline form of 2-acrylamido-2-methylpropane sulfonic acid according to the invention.

The cationic monomer(s) that may be used in the invention may particularly be selected from monomers of the acrylamide, acrylic, vinyl, allyl or maleic type having a phosphonium or quaternary ammonium function. Mention may be made, in particular and in a non-limiting way, of quaternized dimethylaminoethyl acrylate (ADAME), quaternized dimethylaminoethyl methacrylate (MADAME), dimethyldiallylammonium chloride (DADMAC), acrylamido propyltrimethyl ammonium chloride (APTAC) and methacrylamido propyltrimethyl ammonium chloride (MAPTAC). The quaternizing agent may be chosen from alkyl chlorides, dialkyl sulphates or alkyl halides. Preferably, the quaternizing agent is chosen from methyl chloride or diethyl sulphate.

The zwitterionic monomer may be of the type acrylamide, acrylic, vinyl, allyl or maleic having an amine or quaternary ammonium function and an acid function like a carboxylic, sulfonic or phosphoric acid. Mention may be made, specifically and in a non-limiting manner, of dimethylaminoethyl acrylate derivatives, such as 2-((2-(acryloyloxy)ethyl)dimethylammonio)ethane-1-sulfonate, 3-((2-(acryloyloxy)ethyl)dimethylammonio)propane-1-sulfonate, 4-((2-(acryloyloxy)ethyl)dimethylammonio) butane-1-sulfonate, [2-(acryloyloxy)ethyl)] (dimethylammonio) acetate, dimethylaminoethyl methacrylate derivatives such as 2-((2-(methacryloyloxy) ethyl) dimethylammonio) ethane-1-sulfonate, 3-((2-(methacryloyloxy) ethyl) dimethylammonio) propane-1-sulfonate, 4-((2-(methacryloyloxy) ethyl) dimethylammonio) butane-1-sulfonate, [2-(methacryloyloxy) ethyl] (dimethylammonio) acetate, dimethylamino propylacrylamide derivatives such as 2-((3-acrylamidopropyl) dimethylammonio) ethane-1-sulfonate, 3-((3-acrylamidopropyl) dimethylammonio) propane-1-sulfonate, 4-((3-acrylamidopropyl) dimethylammonio) butane-1-sulfonate, [3-(acryloyloxy) propyl] (dimethylammonio) acetate, dimethylamino propyl methylacrylamide derivatives such as 2-((3-methacrylamidopropyl) dimethylammonio) ethane-1-sulfonate, 3-((3-methacrylamidopropyl) dimethylammonio) propane-1-sulfonate, 4-((3-methacrylamidopropyl) dimethylammonio) butane-1-sulfonate and [3-(methacryloyloxy) propyl)] (dimethylammonio) acetate.

Monomers with a hydrophobic nature may also be used in the invention. They are preferably selected from the group consisting of (meth)acrylic acid esters having an alkyl, arylalkyl, propoxylated, ethoxylated, or ethoxylated and propoxylated chain; (meth)acrylamide derivatives having an alkyl, arylalkyl, propoxylated, ethoxylated, ethoxylated and propoxylated, or dialkyl chain; alkyl aryl sulfonates.

When a monomer having a hydrophobic nature is used, the quantity thereof lies advantageously within the range between 0.001 and 3 mol % in relation to the total quantity of monomers.

Monomers with a fluorescent function may also be used in the scope of the invention. A monomer with a fluorescent function may be detected by any appropriate method, for example by fluorimetry with a fixed wavelength fluorimeter. Generally, the monomer having a fluorescent function is detected at the excitation and emission maxima, which can be determined using a scanning fluorimeter.

Those monomers having a fluorescent function are chosen from, for example, monomers comprising sodium sulfonate styrene and sulfonic styrene.

According to the invention, the (co)polymer used may have a linear, branched, cross-linked, star-shaped or comb-shaped structure. These structures may be obtained by the selection of the initiator, transfer agent, polymerization technique, such as controlled radical polymerization known as RAFT (reversible-addition fragmentation chain transfer), NMP (nitroxide-mediated polymerization) or ATRP (atom-transfer radical polymerization), incorporation of structural monomers, or concentration, etc.

Generally, the (co)polymer does not require the development of any particular polymerization method. Indeed, it may be obtained according to polymerization techniques known by a person skilled in the art. It may notably be solution polymerization, gel polymerization, precipitation polymerization, emulsion polymerization (aqueous or inverse), suspension polymerization, reactive extrusion polymerization, or micellar polymerization.

According to a specific embodiment of the invention, the (co)polymer may be post-hydrolyzed. Post-hydrolysis is the reaction of the (co)polymer after polymerization. This step consists in reacting the hydrolyzable functional groups on the nonionic monomers, such as amide or ester functions, with a base. During this (co)polymer post-hydrolysis step, the number of carboxylic acid functions increases. The reaction between the base and the amide or ester functions produces carboxylate groups in the (co)polymer product.

The (co)polymer may be in the form of a liquid, gel or solid when its preparation includes a drying step such as spray drying, tumble drying, drying by electromagnetic radiation (microwave, high frequency), or fluidized bed drying.

According to the invention, the (co)polymer may be linear, structured or crosslinked. Structured (co)polymer denotes a non-linear (co)polymer that has side chains so as to obtain, when this (co)polymer is dissolved in water, a high state of tangling leading to very high viscosities at low gradients.

The (co)polymer may in addition be structured or cross-linked:

by at least one structure agent, which can be chosen from the group comprising unsaturated polyethylenic monomers (having at least two unsaturated functions), such as for example vinyl, allyl, acrylic and epoxy functions and for example mention may be made of methylene-bis-acrylamide (MBA), triallyamine, tetraallylammonium chloride, 1,2-dihydroxyethylene bis-(N-acrylamide), and/or by macroinitiators such as polyperoxides, polyazoics and poly transfer agents such as polymercaptan (co)polymers, and polyols, and/or by functionalized polysaccharides.

The quantity of branching/crosslinking agent in the monomer mixture is advantageously less than 4% by weight relative to the monomer content, more advantageously less than 1%, and even more advantageously less than 0.5%. According to a specific embodiment, it may at least equal to 0.00001% by weight in relation to the monomer content.

According to a specific embodiment, the (co)polymer may comprise at least one LCST group.

According to the general knowledge of a person skilled in the art, a LCST group corresponds to a group whose water solubility for a determined concentration is modified beyond a certain temperature and as a function of the salinity. This is a group having a heating transition temperature defining its lack of affinity with the solvent medium. The lack of affinity with the solvent results in opacification or loss of transparency, which may be due to precipitation, aggregation, gelification, or viscosification of the medium. The minimum transition temperature is known as "LCST" (Lower Critical Solution Temperature). For each concentration of the LCST group, a heating transition temperature is observed. It is greater than the LCST, which is the minimum point in the curve. Below this temperature, the (co)polymer is soluble in water; above this temperature, the (co)polymer loses its solubility in water.

According to a specific embodiment, the (co)polymer may comprise at least one UCST group.

According to the general knowledge of a person skilled in the art, a UCST group corresponds to a group whose water solubility for a determined concentration is modified beyond a certain temperature and as function of the salinity. This is a group having a cooling transition temperature defining its lack of affinity with the solvent medium. The lack of affinity with the solvent results in opacification or loss of transparency, which may be due to precipitation, aggregation, gelification, or viscosification of the medium. The maximum transition temperature is known as "UCST" (Upper Critical Solution Temperature). For each concentration of the UCST group, a cooling transition temperature is observed. It is lower than the UCST, which is the maximum point in the curve. Above this temperature, the (co)polymer is soluble in water; below this temperature, the (co)polymer loses its water solubility.

According to the invention, the (co)polymer has an advantageously high molecular weight. "High molecular weight" denotes molecular weights of at least 1 million g/mol, preferably between 2 and 40 millions g/mol, more preferably between 5 and 30 million g/mol. Molecular weight is understood as average molecular weight by weight.

According to one embodiment of the invention, the copolymer may be obtained by (co)polymerization of at least one water-soluble monomer and at least one monomer of the hydrated crystalline form of 2-acrylamido-2-methylpropane sulfonic acid and/or of one of its salts.

Broadly speaking, unless otherwise indicated, "2-acrylamido-2-methylpropane sulfonic acid in hydrated crystalline form" denotes the acid form and/or the salified form. The same applies to the anionic monomers mentioned in the description of the invention, which may denote the acid and/or salified forms like, for example, for acrylic acid.

The salt form is advantageously obtained from a compound chosen from among an alkali or alkaline earth metal hydroxide, an alkali or alkaline metal earth oxide, ammonia, an amine having the following formula $NR_1R_2R_3$ ($R_1$, $R_2$ and $R_3$ being advantageously hydrocarbon groups, in particular alkyl groups) or an alkali or alkaline earth metal carbonate. A preferred alkaline metal is sodium.

The acid form of a monomer can be salified before and/or during and/or after the (co)polymerization of the monomer or monomers.

The (co)polymer of the invention is preferably water-soluble.

Advantageously, the (co)polymer has a molecular weight of between 5000 and 40,000,000 g/mol, preferably between 1,250,000 and 35,000,000 and even more preferably between 2,750,000 and 30,000,000 g/mol by weight.

The molecular weight is determined by the intrinsic viscosity of the (co)polymer. The intrinsic viscosity may be measured by methods known to the person skilled in the art and may be calculated from lower viscosity values for different (co)polymer concentrations by a graphic method consisting in recording the lower viscosity values (y-axis) over the concentration (x-axis) and extrapolating the curve to zero concentration. The intrinsic viscosity value is recorded on the y-axis or using the least squares method. The molecular weight may then be determined by the Mark-Houwink equation:

$$[\eta] = K\,M^{\alpha}$$

$[\eta]$ represents the intrinsic viscosity of the (co)polymer determined by the method for measuring viscosity in solution.

K represents an empirical constant.

M represents the molecular weight of the (co)polymer.

$\alpha$ represents the Mark-Houwink coefficient.

K and $\alpha$ depend on the specific (co)polymer-solvent system.

Another feature of the invention relates to the use of (co)polymers made from the hydrated crystalline form of 2-acrylamido-2-methylpropane sulfonic acid or at least one of its salts. In these (co)polymers, 2-acrylamido-2-methylpropane sulfonic acid may be partially neutralized before, during, or after the (co)polymerization of 2-acrylamido-2-methylpropane sulfonic acid. More precisely, the invention relates to the use of these (co)polymers in the oil and gas, hydraulic fracturing, paper, water treatment, construction, mining, cosmetics, textile, or detergent industry. Preferably, the (co)polymers are used in the field of enhanced oil and gas recovery.

The invention and the benefits that flow from it will be clearer upon reading the following figures and examples, given to illustrate the invention and not to limit it in any way.

EXAMPLE EMBODIMENTS OF THE INVENTION

Example 1: Synthesis of 2-acrylamido-2-methylpropane sulfonic acid

To a stirred 2000-mL jacketed reactor, 1522 grams of acrylonitrile was added containing 0.4% of water by weight and 180 grams of fuming sulfuric acid titrating at 104% $H_2SO_4$ (18% Oleum). The mixture was stirred for 1 hour and cooled via the reactor jacket, which held the temperature of the sulfonating mixture at −20° C.

To the previous sulfonating mixture, 97 grams of isobutylene was added, at a flow rate of 1.6 grams/minute.

The temperature of the mixture was controlled at 45° C. while isobutylene was added. The particles of 2-acrylamido-2-methylpropane sulfonic acid precipitate in the mixture and the solid content was about 20% by weight. The reaction mixture was filtered on a Büchner filter and dried under vacuum at 50° C. The solid obtained was 2-acrylamido-2-methylpropane sulfonic acid; it was present in the form of a very fine white powder.

Figure 10:
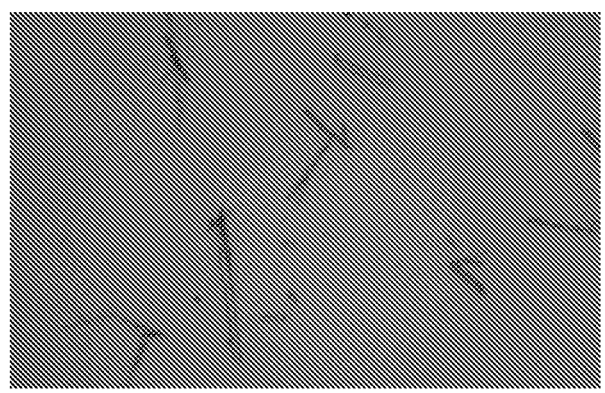
FIG. 10 corresponds to the optical microscope observation of the crystals obtained according to example 1.
Figure 12:
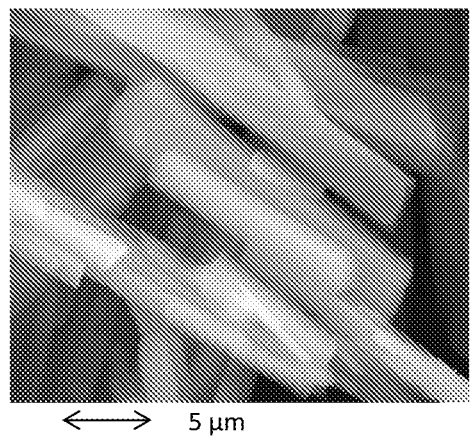
FIG. 12 corresponds to the scanning electron microscope observation of the crystals obtained according to example 1.

From observations made with an optical microscope (FIG. 10) and a scanning electron microscope (FIG. 12), the crystals were needle-shaped.

Example 2: Formation of the Hydrated Crystalline Form of 2-acrylamido-2-methylpropane sulfonic acid To a 2000-mL jacketed reactor, 500 grams of 2-acrylamido-2-methylpropane sulfonic acid obtained in example 1 and 460 grams of sulfuric acid at a concentration of 10% $H_2SO_4$ were added.

250 mg of 4-hydroxy-2,2,6,6-tetramethylpiperidin-1-oxyl was added to the preceding mixture.

The mixture was stirred for 10 minutes, at 20° C., to form suspension A.

Suspension A was heated to a temperature of 60° C. and maintained at this temperature for 20 minutes to form solution B.

Solution B was cooled to a temperature of 10° C. The cooling time between 60° C. and 10° C. was 6 hours. Suspension C of crystals of 2-acrylamido-2-methylpropane sulfonic acid was obtained. Suspension C was filtered on a vertical Robatel centrifugal dryer. A solid of composition 1 was obtained, containing 80% by weight of 2-acrylamido-2-methylpropane sulfonic acid crystals.

Figure 11:
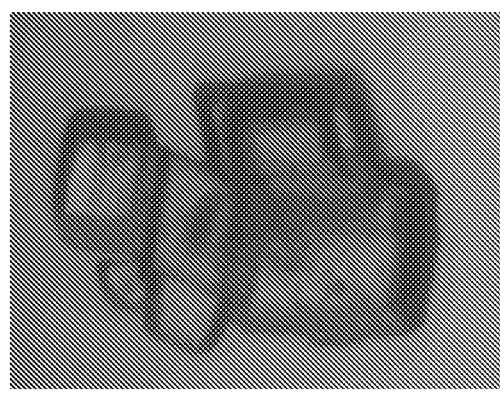
FIG. 11 corresponds to the optical microscope observation of the crystals obtained according to example 2.
Figure 13:
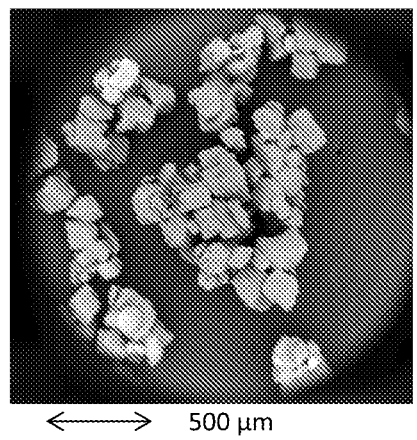
FIG. 13 corresponds to the scanning electron microscope observation of the crystals obtained according to example 2.
Figure 2:
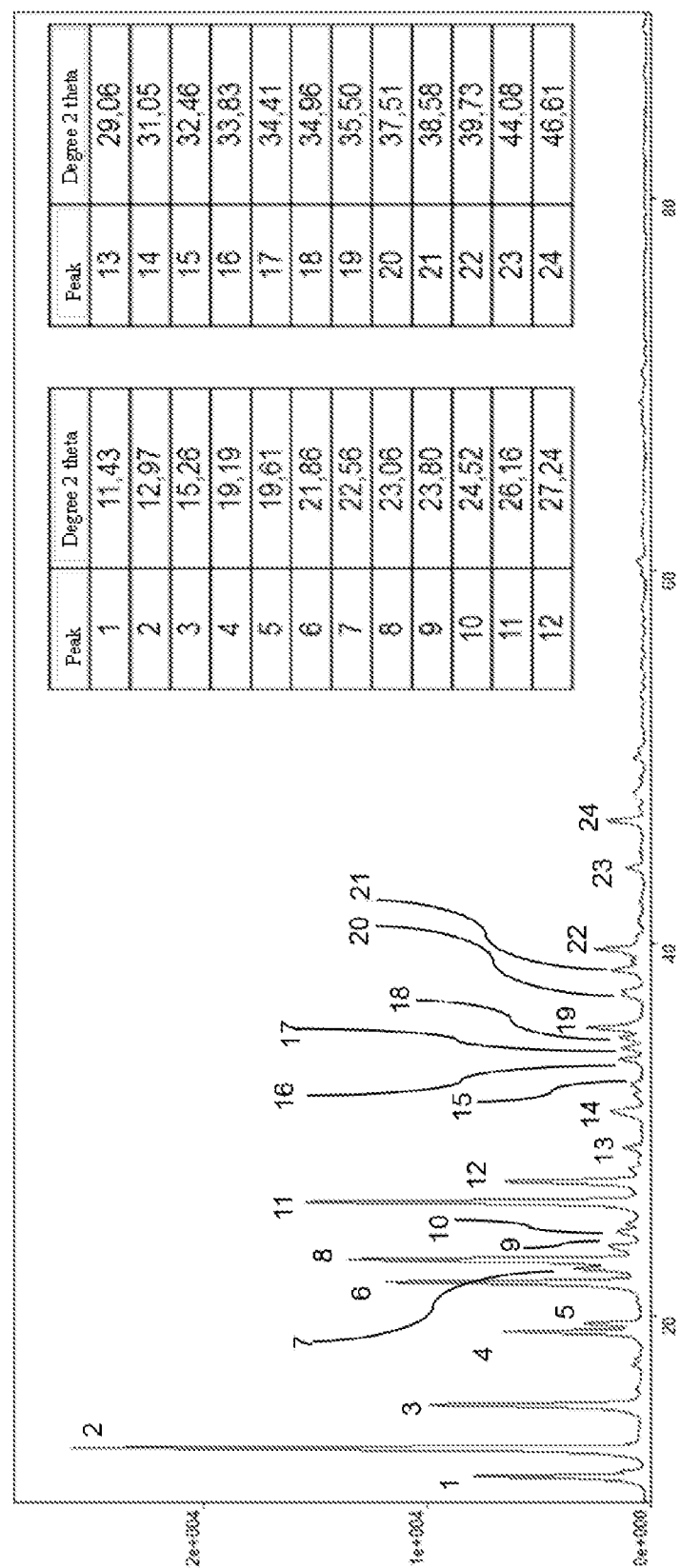
FIG. 2 illustrates the X-ray diffraction diagram of the crystals obtained according to example 1.

From observations made with an optical microscope (FIG. 11) and a scanning electron microscope (FIG. 13), the crystals were cubic-shaped.

Example 3: NMR Analysis of Products from Examples 1 and 2

The 2-acrylamido-2-methylpropane sulfonic solid obtained in example 1 and its hydrated crystalline form obtained in example 2 were analyzed by proton nuclear magnetic resonance (NMR).

The samples were dissolved in $D_2O$. The Bruker NMR machine had a frequency of 400 MHz, and was equipped with a 5 mm BBO BB-$^1$H probe.

Figure 1:
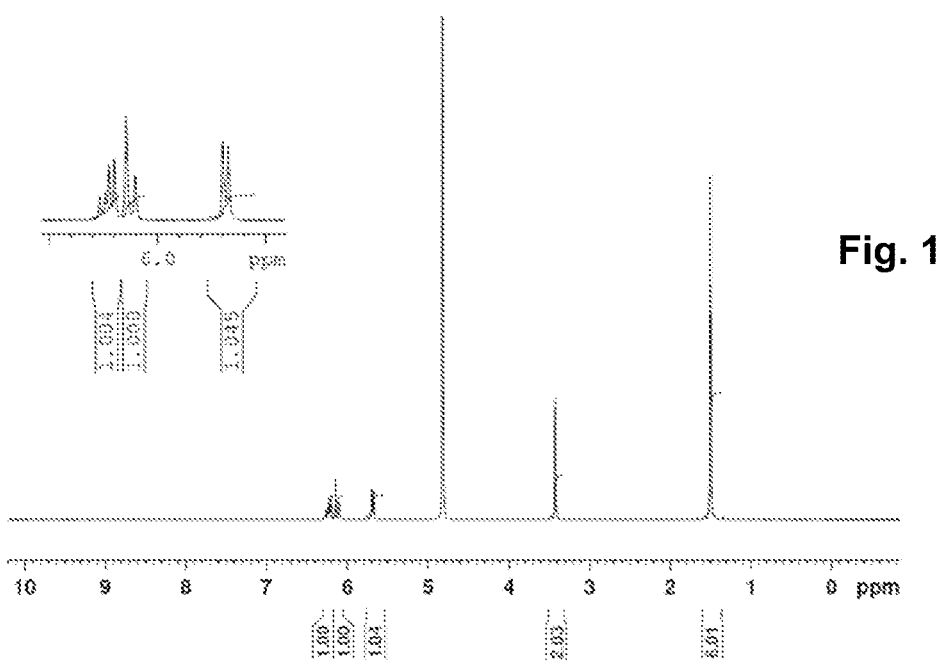
FIG. 1 illustrates the proton NMR spectrum of the 2-acrylamido-2-methylpropane sulfonic acid crystals obtained according to examples 1 and 2.

The two proton spectra (FIG. 1) were identical and the peak assignments conformed to the molecular structure of 2-acrylamido-2-methylpropane sulfonic acid.

Example 4: X-Ray Diffraction Analysis

The solids obtained in examples 1 and 2 were previously ground to form powders and were analyzed by X-ray diffraction over an angular range from 10 to 90°. The equipment used was a Rigaku miniflex II diffractometer equipped with a copper source.

Figure 3:
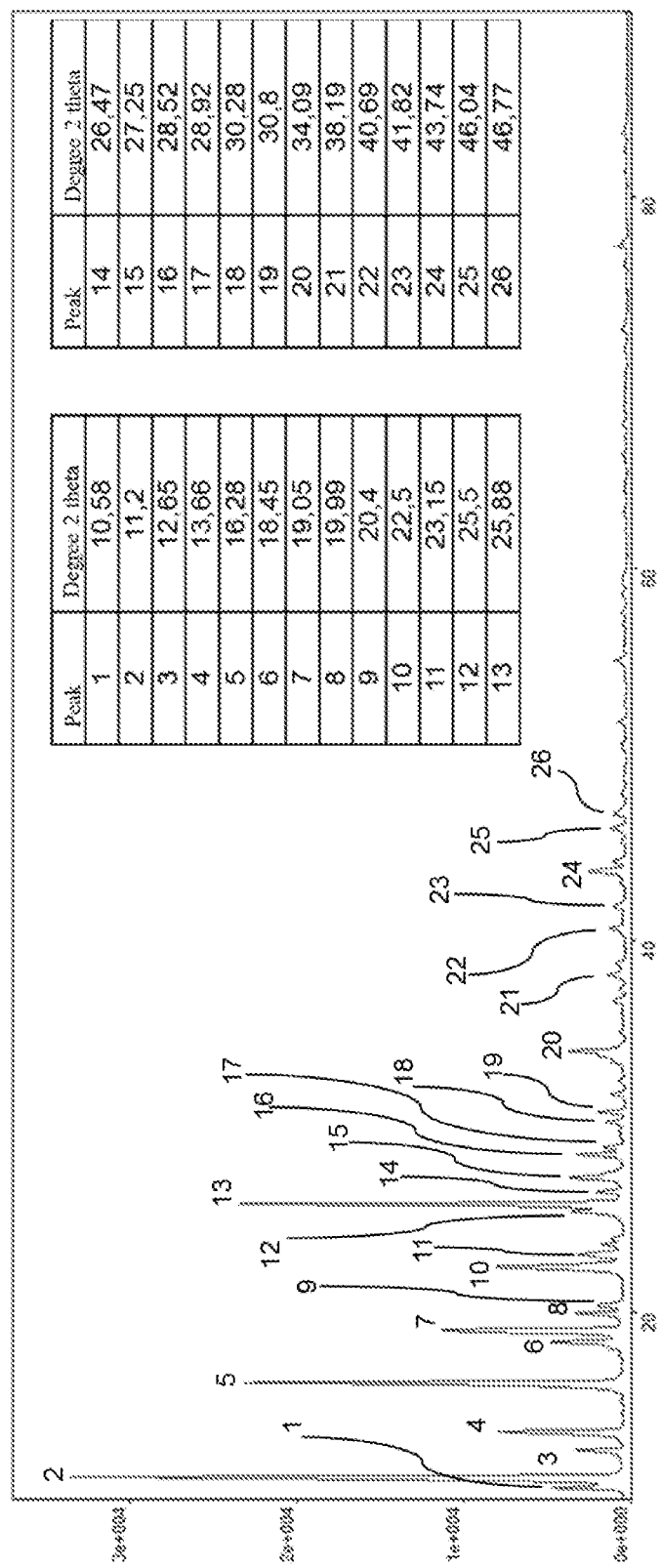
FIG. 3 illustrates the X-ray diffraction diagram of the crystals obtained according to example 2.

We observed that the solid obtained from example 2 (FIG. 3) has a 2-theta X-ray diffraction diagram with the following characteristic peaks:

10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° 2-Theta degrees (+/−0.1°).

Example 5: Fourier Transform Infrared Measurement

The equipment for Fourier transform infrared measurement was the Perkin Elmer Spectrum 100, whose precision is 8 $cm^{-1}$.

The solids obtained in examples 1 and 2 were sieved at 100 μm. The particles remaining on the sieve were dried and put in the oven at 60° C. for at least 4 hours.

10 mg of solid was weighed precisely and mixed with 500 mg of potassium bromide (KBr). The mixture was then compacted in a hydraulic press under a pressure of at least 10 bars.

Figure 5:
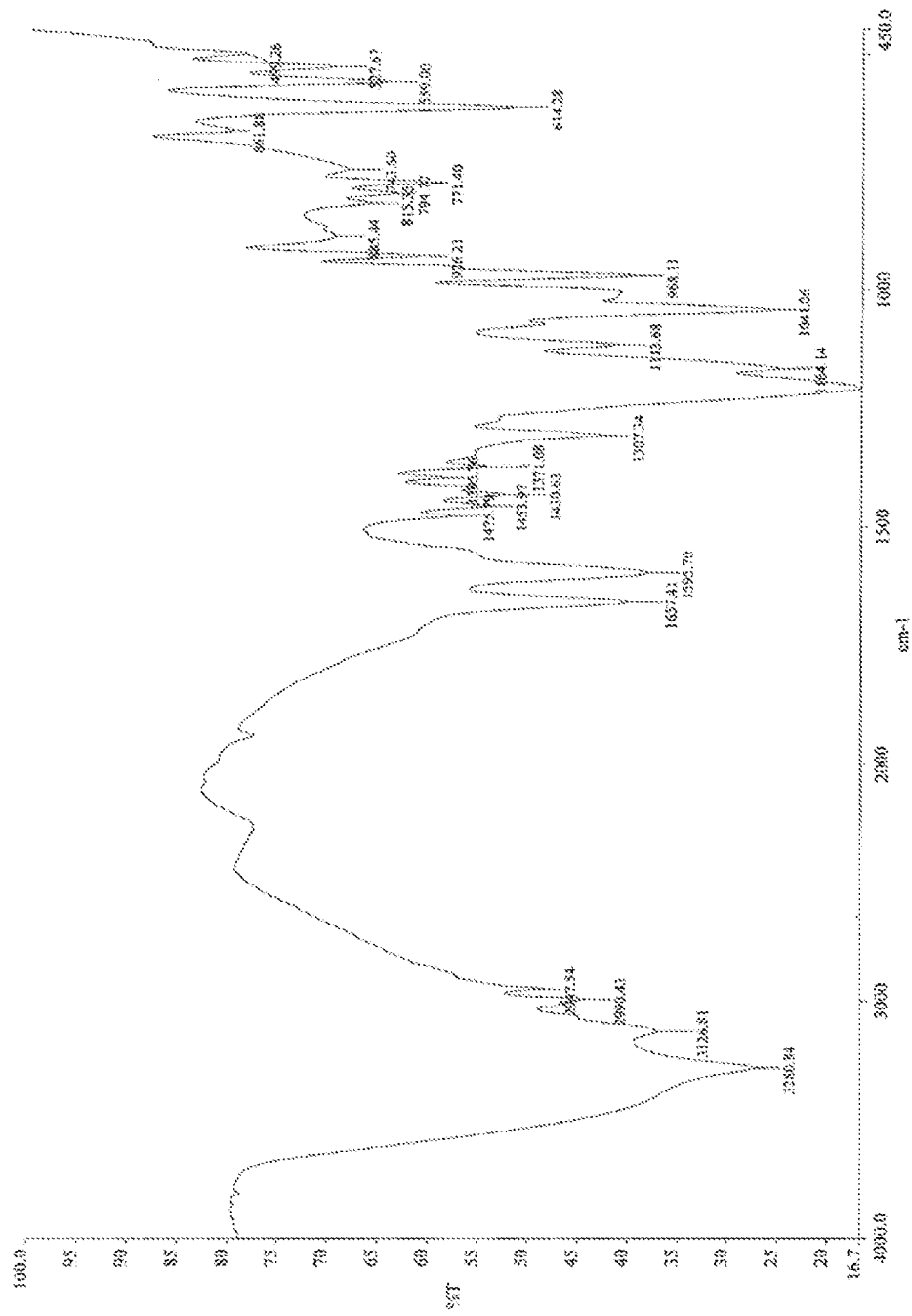
FIG. 5 illustrates the X-ray diffraction diagram of the crystals obtained according to example 2.

We observed that the following bands (FIG. 5) are characteristic of the hydrated crystalline form of 2-acrylamido-2-methylpropane sulfonic acid:

3280 $cm^{-1}$, 3126 $cm^{-1}$, 1657 $cm^{-1}$, 1595 $cm^{-1}$, 1453 $cm^{-1}$, 1395 $cm^{-1}$, 1307 $cm^{-1}$, 1205 $cm^{-1}$, 1164 $cm^{-1}$, 1113 $cm^{-1}$, 1041 $cm^{-1}$, 968 $cm^{-1}$, 885 $cm^{-1}$, 815 $cm^{-1}$, 794 $cm^{-1}$.

Figure 4:
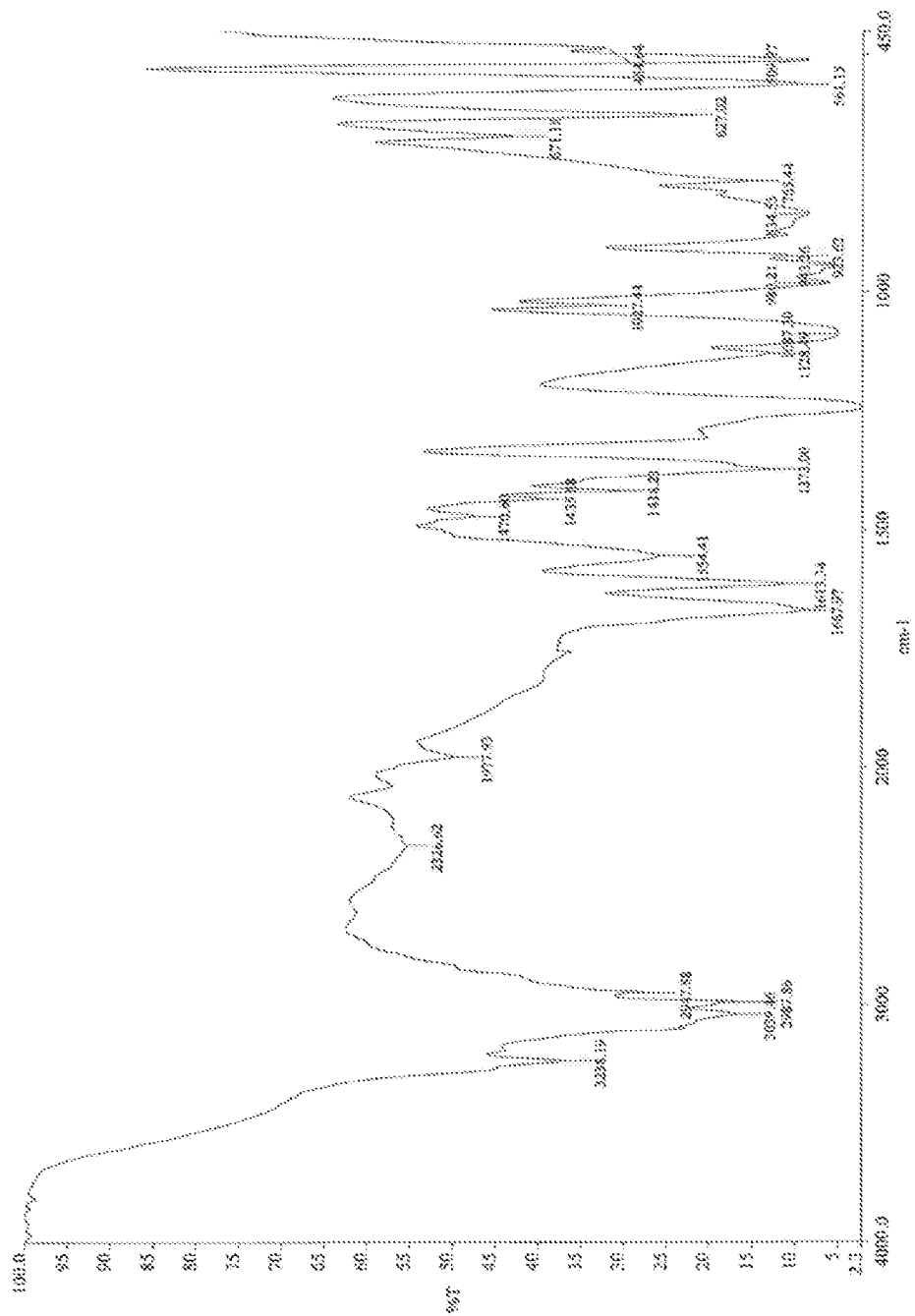
FIG. 4 illustrates the Fourier transform infrared spectrum of the crystals obtained in example 1.

The infrared spectrum of the solid according to example 1 (FIG. 4) did not present the same peaks.

Example 6: Differential Scanning Calorimetry (DSC)

The device used was a DSC131 EVO by Setaram.

The solids obtained in examples 1 and 2 were analyzed with a 10° C./minute heating ramp under a flow of nitrogen. The initial temperature was 30° C.; the product was heated to 220° C.

The thermogram of the crystals in example 1 (FIG. 6) showed a thermal effect at a temperature of 191.5° C., which is generally considered as the melting/degradation point of 2-acrylamido-2-methylpropane sulfonic acid.

Figure 7:
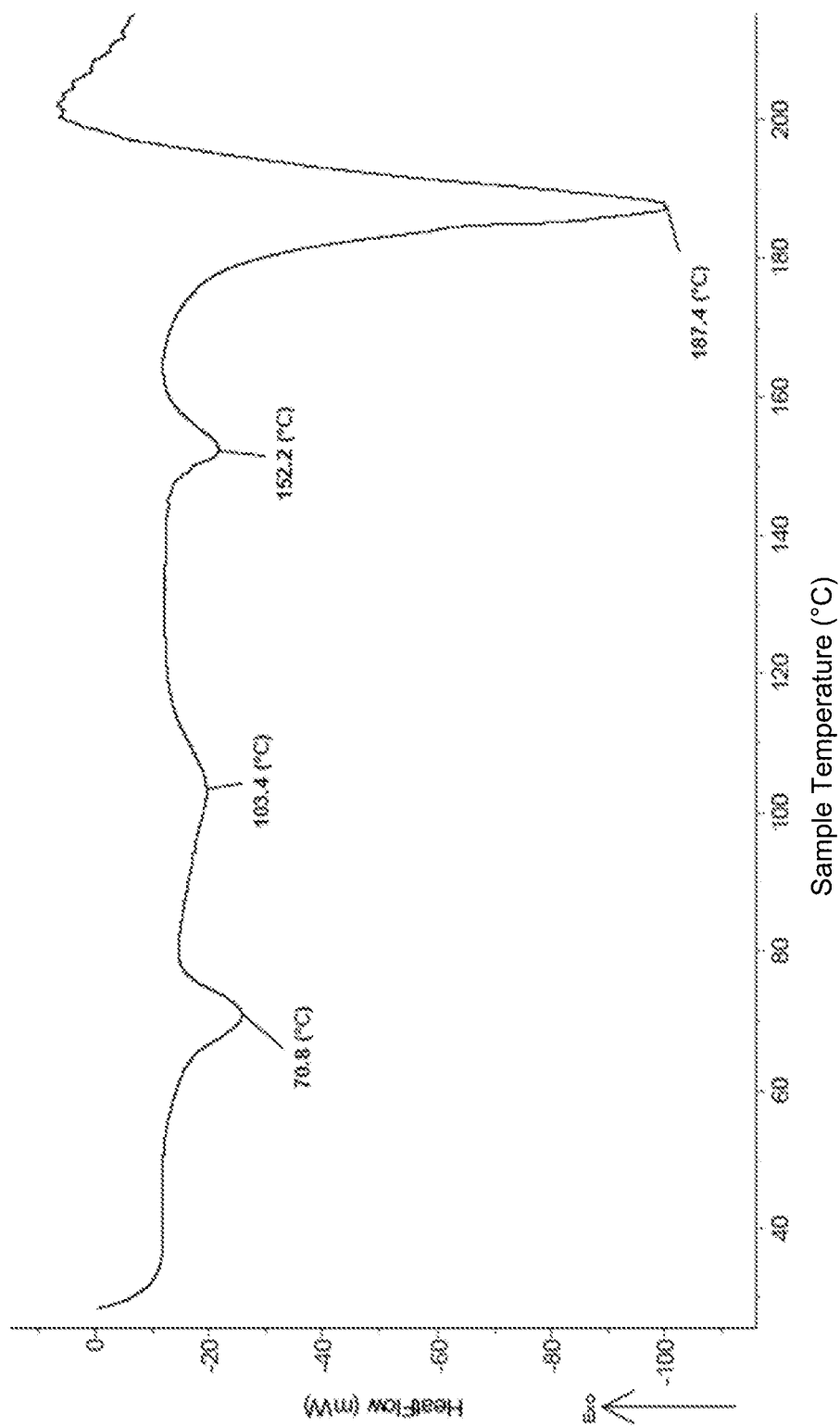
FIG. 7 illustrates the thermogram of the crystals obtained according to example 2.

The thermogram of the crystals from example 2 (FIG. 7) showed 3 additional thermal phenomena visible at 70.8; 103.4 and 152.2° C. The peak at 187.4° C. is related to the degradation of the molecule of 2-acrylamido-2-methylpropane sulfonic acid.

Figure 6:
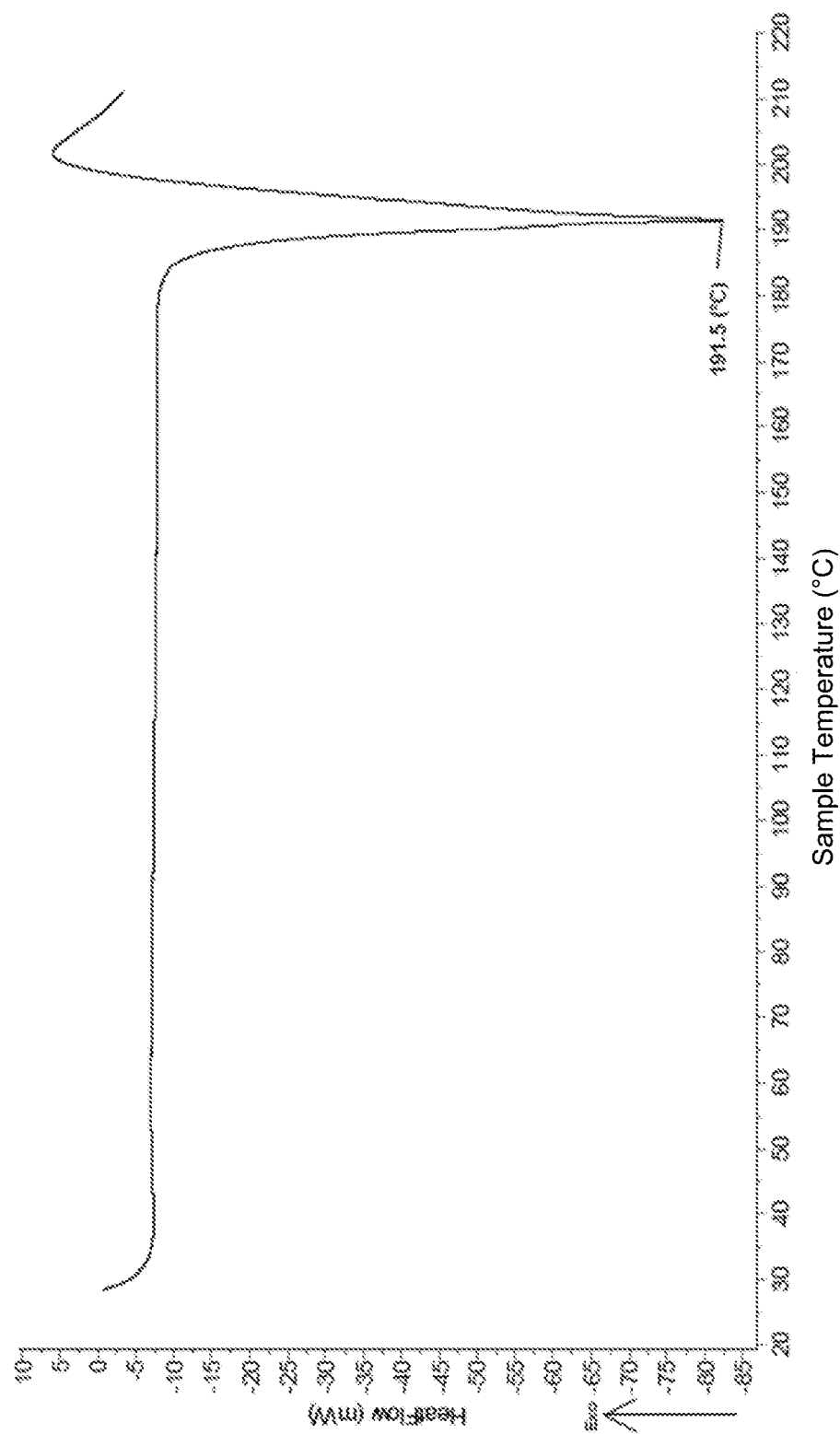
FIG. 6 illustrates the thermogram of the crystals obtained according to example 1.

As a comparison, the thermogram of the crystals from example 1 did not present a degradation peak at 191.5° C. (FIG. 6).

Example 7: Acid-Base Titration

To a 1000-mL beaker, 500 mL of demineralized water and 100 g of the obtained from example 1 were added. A magnetic bar was added to be able to mix the solution.

A graduated burette was filled with 30% sodium hydroxide.

A pH meter was added to be able to monitor the pH during the sodium hydroxide addition.

Initially the pH of the aqueous solution was less than 1 Sodium hydroxide was added until a pH of 7 was obtained.

64 g of 30% sodium hydroxide was added.

The molar mass of 2-acrylamido-2-methylpropane sulfonic acid was 207 g/mol. Calculating the equivalence point showed that the solid obtained in example 1 contained 99% by weight of 2-acrylamido-2-methylpropane sulfonic acid (titration of the acid function).

The solid obtained in example 2 was titrated using the same protocol. 59 g of sodium hydroxide was added to 100 g of the solid obtained from example 2. Calculating the equivalence point showed that the solid obtained in example 2 contained 92% by weight of 2-acrylamido-2-methylpropane sulfonic acid.

The remaining 8% was water. This 2-acrylamido-2-methylpropane sulfonic acid/$H_2O$ mass ratio (92/8) corresponded to a 1:1 molar ratio.

The solid obtained in example 2 was therefore a hydrated crystalline form of 2-acrylamido-2-methylpropane sulfonic acid.

Example 8: Measurement of the Minimum Ignition Energy (MIE)

Minimum ignition energy was measured according to standard NF EN 13821.

The explosimeter was a vertical Hartmann tube. The dust dispersion system was a mushroom system.

The total induction was less than 25 microhenry. The discharge voltage was comprised between 5 kV and 15 kV. The electrodes were made of brass and spaced at least 6 mm apart.

Different energies and dispersed mass were tested and summarized in the following tables.

It appears clearly that the hydrated crystalline form presents a substantially lower explosion risk than the needle-shaped form obtained in example 1.

TABLE 1

Determination of the solid MIE from example 1

| Energy (mJ) | Mass of dispersed solid (g) | Number of dispersions | Ignition? Yes (Y) No (N) | Flame | Pressure |
|---|---|---|---|---|---|
| 1000 | 0.5 | 2 | Y | Small | Small |
| 500 | 0.5 | 3 | Y | Average | Average |
| 300 | 0.5 | 3 | Y | Average | Average |
| 100 | 0.5 | 20 | N | | |
| 200 | 0.5 | 20 | N | | |
| 200 | 1 | 20 | N | | |
| 200 | 2 | 20 | N | | |
| 200 | 3 | 7 | Y | Average | Small |
| 100 | 3 | 20 | N | | |
| 100 | 5 | 20 | N | | |
| 100 | 7 | 20 | N | | |
| 100 | 10 | 20 | N | | |
| 100 | 1 | 20 | N | | |
| 100 | 2 | 20 | N | | |

TABLE 2

Determination of the solid MIE from example 2

| Energy (mJ) | Mass of dispersed solid (g) | Number of dispersions | Ignition? Yes (Y) No (N) | Flame | Pressure |
|---|---|---|---|---|---|
| 1000 | 0.5 | 20 | N | | |
| 1000 | 1 | 20 | N | | |
| 1000 | 2 | 20 | N | | |
| 1000 | 3 | 20 | N | | |
| 1000 | 5 | 20 | N | | |
| 1000 | 7 | 20 | N | | |
| 1000 | 10 | 20 | N | | |
| 1000 | 15 | 13 | Y | Small | Average |
| 500 | 15 | 20 | N | | |
| 500 | 20 | 20 | N | | |
| 500 | 10 | 20 | N | | |
| 500 | 7 | 20 | N | | |
| 500 | 5 | 20 | N | | |
| 500 | 3 | 20 | N | | |
| 500 | 2 | 20 | N | | |
| 500 | 1 | 20 | N | | |
| 500 | 0.5 | 20 | N | | |

Example 9: Particle Size Measurement

The solids obtained in examples 1 and 2 were analyzed by laser diffraction to determine their particle size distribution.

The equipment used was a Cilas 1190.

Figure 8:
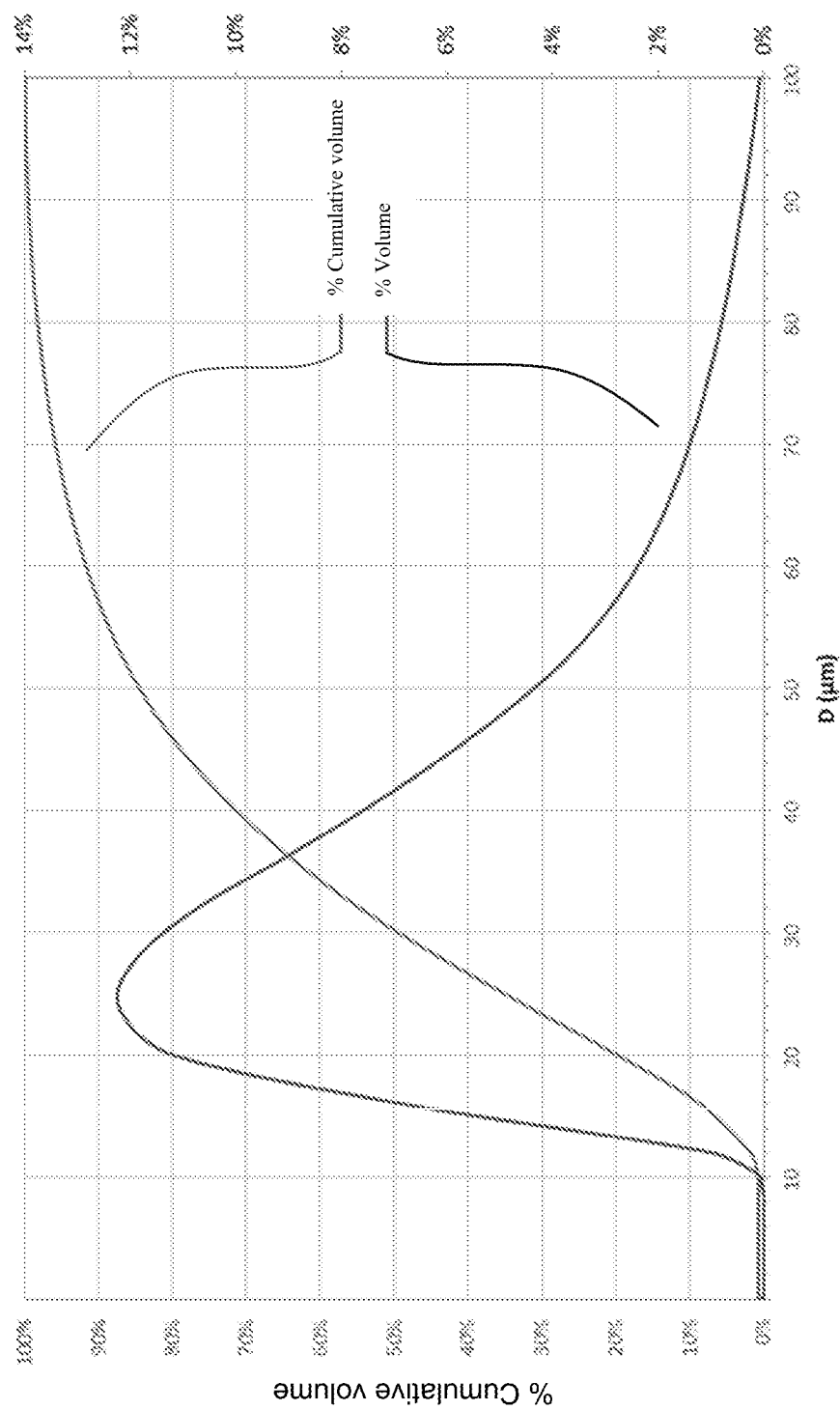
FIG. 8 illustrates the particle size graph of the crystals obtained according to example 1.

For the crystals in example 1, the $d_{50}$ value was about 40 μm and 90% of the particles were smaller than 200 μm (FIG. 8).

Figure 9:
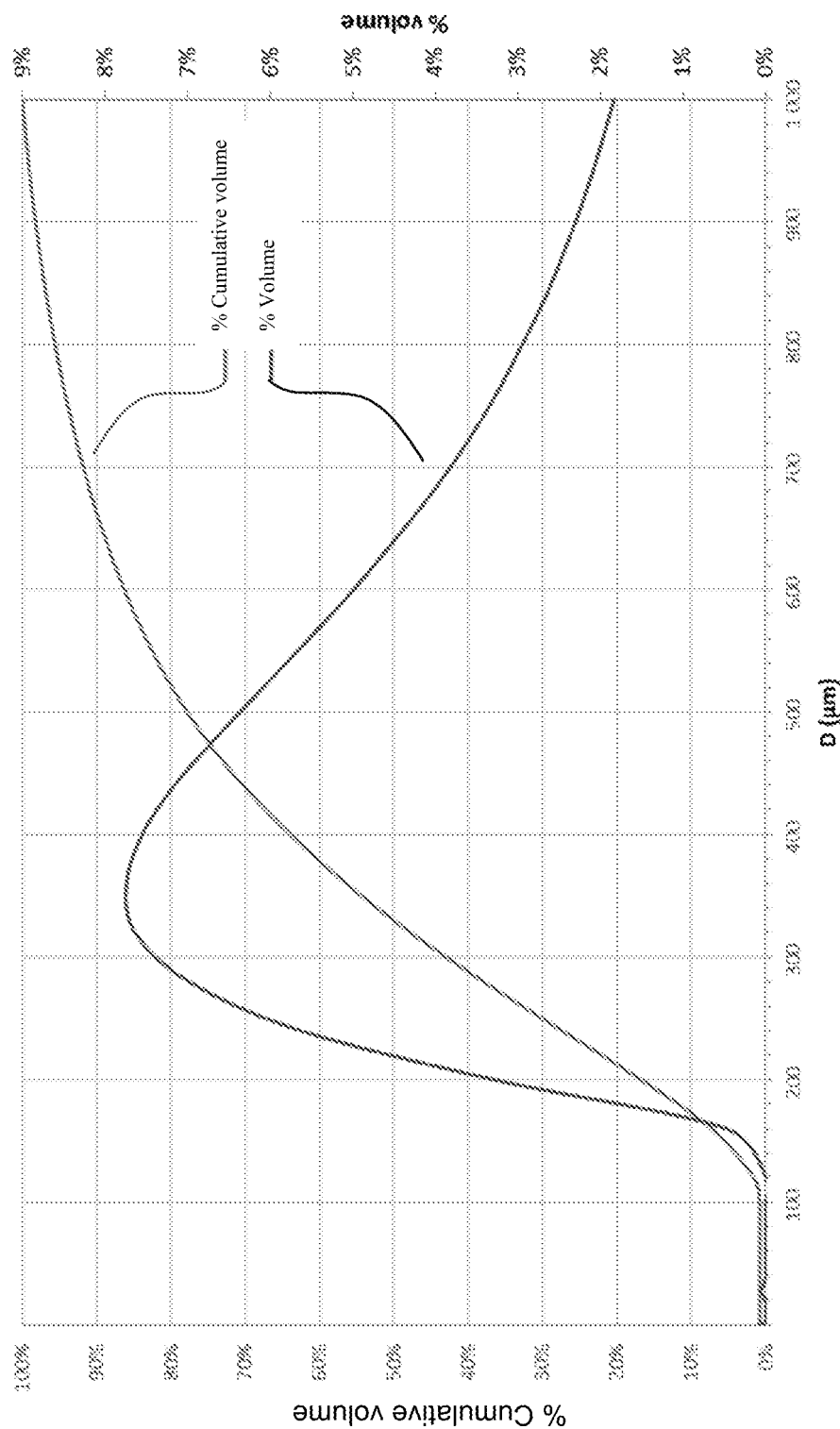
FIG. 9 illustrates the particle size graph of the crystals obtained according to example 2.

For the crystals in example 2, the $d_{50}$ value was about 600 μm and 90% of the particles were smaller than 1500 μm (FIG. 9). The crystals contained less than 10% of particles smaller than 300 μm.

Example 10: Measurement of Specific Surface Area

The solids obtained in examples 1 and 2 were degassed at ambient temperature for 24 hours.

The device for measuring specific surface area by sorptometry was a TriStar II Micromeritics device coupled with a Micromeritics Smart VacPrep. The measurement temperature was −196° C.

TABLE 3

Specific surface area of 2-acrylamido-2-methylpropane sulfonic acids

| Origin of the 2-acrylamido-2-methylpropane sulfonic acid | Specific surface area (m²/g) |
|---|---|
| Example 1 (counter-example) | 1.32 +/− 0.14 |
| Example 2 (invention) | 0.06 +/− 0.01 |

Example 11: Preparation Protocol for the Sodium Salt of the Hydrated Crystalline Form of 2-acrylamido-2-methylpropane sulfonic acid To a jacketed 2000-mL reactor equipped with a condenser, a pH meter and a stirrer, 500 grams of the hydrated crystalline form of acrylamido-2-methylpropane sulfonic acid from example 2 and 770 grams of water were added. The mixture had a pH of less than 1.

A solution of 50% concentration by weight sodium hydroxide was prepared in a dropping funnel. The caustic solution was added to the reaction mixture for 120 minutes. The temperature was controlled to be less than 30° C.

During the sodium hydroxide addition, the pH remained under 5.

175 grams of 50% concentration by weight sodium hydroxide solution was added.

The mixture obtained was a solution of the 2-acrylamido-2-methylpropane sulfonic acid sodium salt at a concentration of 35% by weight.

Example 12 Preparation of Copolymer P1 of Acrylamide/2-Acrylamido-2-Methylpropane Sulfonic Acid of Hydrated Crystalline Form (75/25 Mole %)

549.5 g of deionized water, 520.5 of acrylamide in 50% solution, 97.6 g of 50% sodium hydroxide solution, 16.2 g of urea and 316.2 g of 2-acrylamido-2-methylpropanesulfonic acid crystals obtained in Example 2g are added to a 2000 ml beaker.

The solution thus obtained is cooled between 0 and 5° C. and transferred to an adiabatic polymerization reactor, nitrogen bubbling is carried out for 30 minutes to remove any trace of dissolved oxygen.

Then added in the reactor:

0.75 g of 2,2'-azobisisobutyronitrile, 1.5 ml of a solution containing 5 g/l of 2,2'-azobis [2-(2-imidazolin-2-yl) propane dihydrochloride], 1.5 ml of a solution containing 3 g/l of sodium hypophosphite, 2.25 ml of a solution containing 1 g/l of tert-butyl hydroperoxide, 2.25 ml of a 1 g/l solution of ammonium sulfate and iron (II) hexahydrate (Mohr salt).

After a few minutes the nitrogen inlet is closed and the reactor is closed. The polymerization reaction takes place for 1 to 5 hours until a peak temperature is reached. The rubbery gel obtained is chopped into particles with a size of between 1 and 6 mm.

The gel is then dried and milled to obtain the polymer in powder form.

Example 13 Preparation of Copolymer P'1 of Acrylamide/2-Acrylamido-2-Methylpropanesulfonic Acid that is not the Hydrated Crystalline Form (75/25 Mole %)

The copolymer is prepared as in Example 12, replacing the crystalline form 2-acrylamido-2-methylpropane sulfonic acid hydrate (Example 2) with the non hydrated crystalline form of 2-acrylamido-2-methylpropanesulfonic acid obtained in Example 1.

Figure 14:
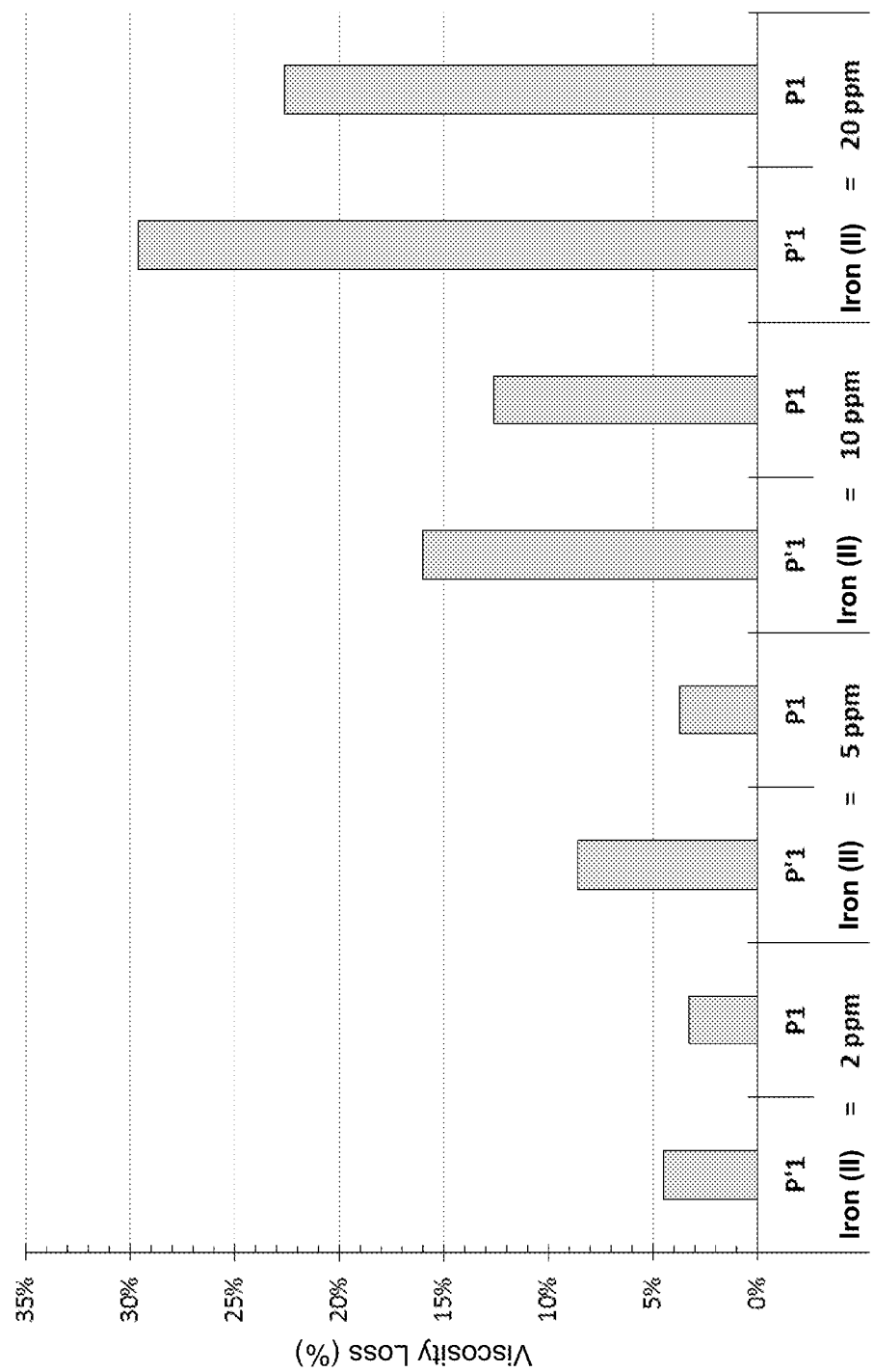
FIG. 14 illustrates the loss of viscosity as a function of ATBS form and iron content for a copolymer.

Example 14 Measurement of the Resistance to Chemical Degradation of Solutions of Copolymers P1 and P'1 of Equivalent Molecular Weight Resistance to chemical degradation tests of polymers P1 and P'1 with a molecular weight of 9 million were carried out under aerobic conditions in the presence of different concentrations of iron (II) (2, 5, 10 and 20 ppm) in a brine composed of water, 37000 ppm NaCl, 5000 ppm $Na_2SO_4$ and 200 ppm $NaHCO_3$. These tests were carried out on a polymer prepared from the non-crystalline form of 2-acrylamido-2-methylpropanesulfonic acid or of at least one of its salts (P'1) and on a polymer prepared from the crystalline form of 2-acrylamido-2-methylpropanesulfonic acid or at least one of its salts (P1). Both polymers have the same chemical composition. The results obtained after 24 hours of bringing the polymer solution into contact with the contaminant are shown in FIG. 14.

We can observe that, for each concentration of iron (II), the polymer P1 loses less viscosity than the polymer P'1 equivalent.

Figure 15:
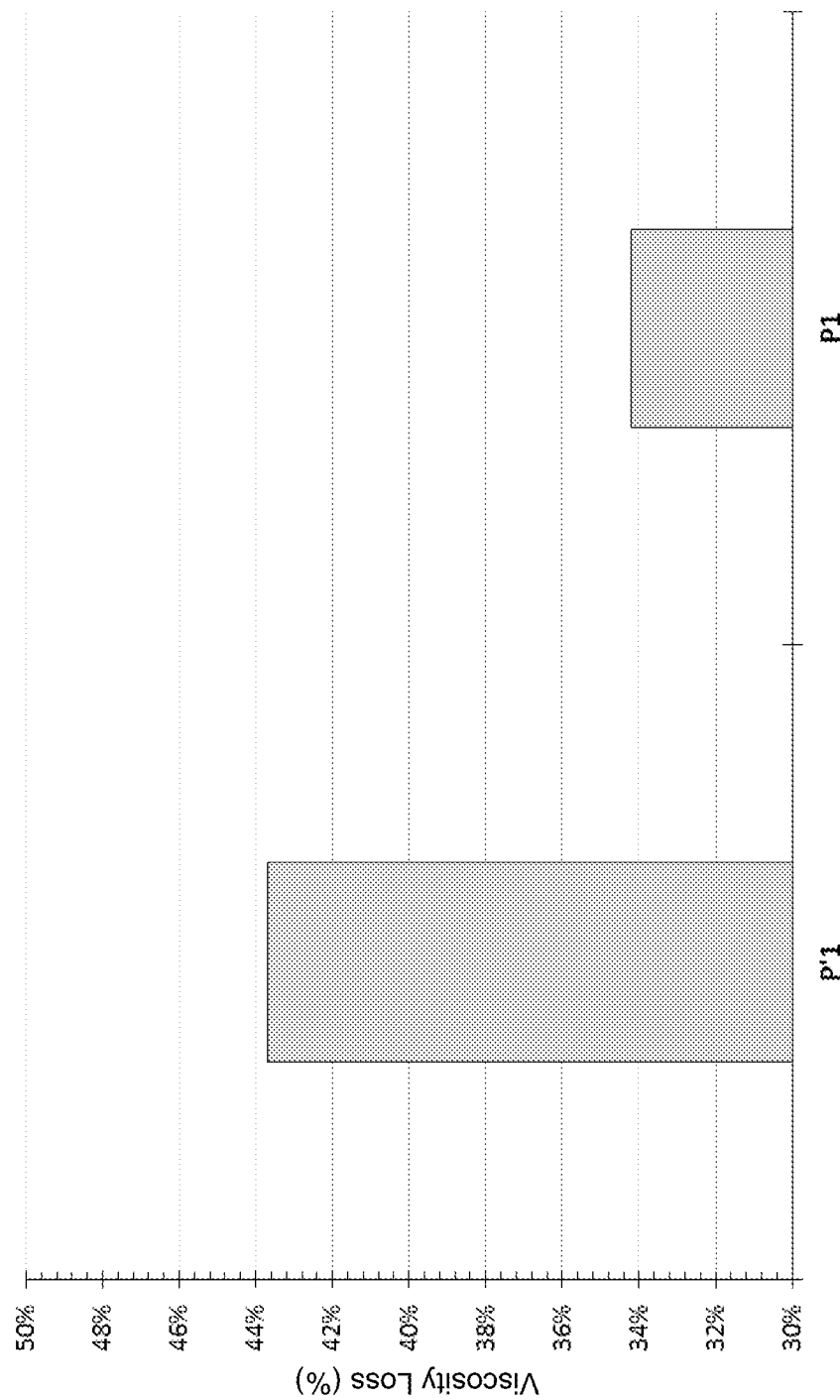
FIG. 15 illustrates the viscosity loss as a function of ATBS form at 90° C. aging for a copolymer.

Example 15 Measurement of Resistance to Thermal Degradation of Solutions of Polymers of Equivalent Molecular Weight Tests of resistance to thermal degradation of polymers P1 and P'1 with a molecular weight of 9 million were carried out anaerobically at an active concentration of 2000 ppm in a brine composed of water, 30000 ppm of NaCl and 3000 ppm $CaCl_2.2H_2O$. These tests were carried out on a polymer made from the non-crystalline form of 2-acrylamido-2-methylpropanesulfonic acid or at least one of its salts (P'1) and on a polymer made from the crystalline form of 2-acrylamido-2-methylpropanesulfonic acid or at least one of its salts (P1). Both polymers have the same chemical composition. The polymer solutions were aged for 6 months at 90° C. The results obtained are shown in FIG. 15 in terms of loss of viscosity. We can observe that the polymer P1 loses less viscosity than the polymer P'1 equivalent.

Example 16 Preparation of Homopolymers P2 from the Hydrated Crystalline Form of 2-acrylamido-2-methylpropanesulfonic acid 390.5 g of deionized water, 262 g of 50% sodium hydroxide solution and 847.5 g of 2-acrylamido-2-methylpropanesulfonic acid crystals obtained in Example 2 are added to a 2000 ml beaker.

The solution thus obtained is cooled between 5 and 10° C. and transferred to an adiabatic polymerization reactor, a nitrogen bubbling is carried out for 30 minutes to remove any trace of dissolved oxygen.

Then added in the reactor:

0.45 g of 2,2'-azobisisobutyronitrile, 1.5 ml of a solution containing 2.5 g/l of 2,2'-azobis [2-(2-imidazolin-2-yl) propane dihydrochloride], 1.5 ml of a 1 g/l solution of sodium hypophosphite, 1.5 ml of a solution containing 1 g/l of tert-butyl hydroperoxide, 1.5 ml of a 1 g/l solution of ammonium sulfate and iron (II) hexahydrate (Mohr salt).

After a few minutes the nitrogen inlet is closed and the reactor is closed. The polymerization reaction takes place for 2 to 5 hours until a peak temperature is reached. The rubbery gel obtained is chopped and dried to obtain a coarse powder which is itself ground and sieved to obtain the polymer in powder form.

Example 17 Preparation of Homopolymers P'2 from 2-Acrylamido-2-Methylpropane Sulfonic Acid that is not the Hydrated Crystalline Form The polymers are prepared as in Example 16, replacing the hydrated crystalline form of 2-acrylamido-2-methylpropanesulfonic acid with 2-acrylamido-2-methylpropanesulfonic acid synthesized in example 1 that is not the hydrated crystalline form.

Example 18 Measurement of Resistance to Chemical Degradation of Solutions of Polymers P2 and P'2

Figure 16:
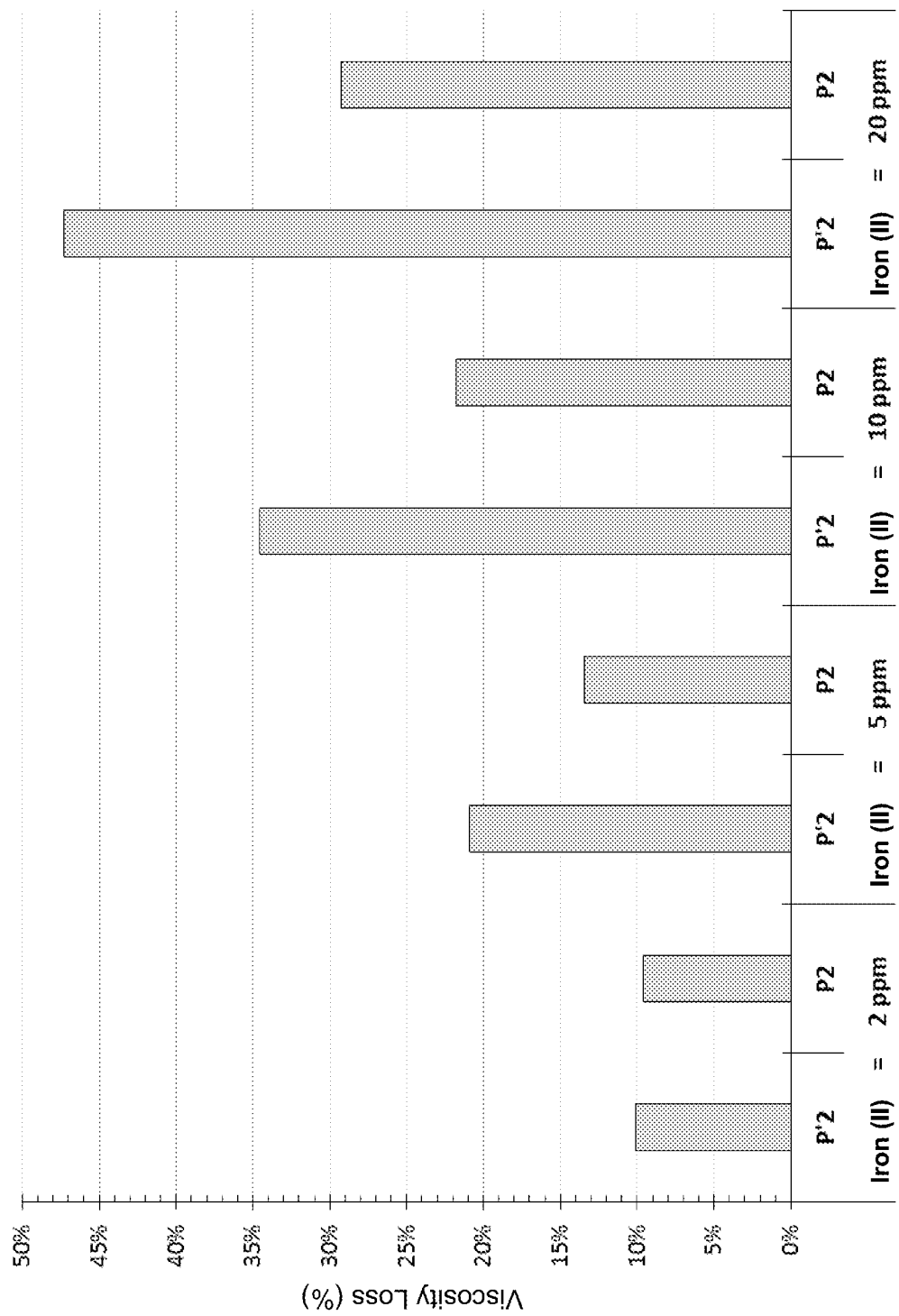
FIG. 16 illustrates the loss of viscosity as a function of ATBS form and iron content for a homopolymer.

Resistance tests to chemical degradation of polymers P2 and P'2 with a molecular weight of 5.3 million Da were performed under aerobic conditions in the presence of various iron (II) concentrations (2, 5, 10 and 20 ppm) in brine composed of water, 37000 ppm NaCl, 5000 ppm $Na_2SO_4$ and 200 ppm $NaHCO_3$. These tests were carried out on a polymer prepared from the non-crystalline form of 2-acrylamido-2-methylpropanesulfonic acid or of at least one of its salts (P'2) and on a polymer prepared from the crystalline form of 2-acrylamido-2-methylpropanesulfonic acid or at least one of its salts (P2). Both polymers have the same chemical composition. The results obtained after 24 hours of bringing the polymer solution into contact with the contaminant are shown in FIG. 16.

We can observe that for each iron (II) concentration, the polymer P2 loses less viscosity than the equivalent polymer P'2.

Example 19 Preparation of Post Hydrolyzed Copolymer P3 of acrylamide/2-acrylamido-2-methylpropane sulfonic acid of Hydrated Crystalline Form (75/25 Mole %)

In a 2000 ml beaker are added 761.9 g of deionized water, 574.2 g of acrylamide in 50% solution, 35.9 g of 50% sodium hydroxide solution, 11.7 g of urea and 116.3 g 2-acrylamido-2-methylpropanesulfonic acid crystals obtained in Example 2.

The solution thus obtained is cooled between 0 and 5° C. and transferred to an adiabatic polymerization reactor, nitrogen bubbling is carried out for 30 minutes to remove any trace of dissolved oxygen.

Then added in the reactor:

0.45 g of 2,2'-azobisisobutyronitrile, 1.5 ml of a solution containing 5 g/l of 2,2'-azobis [2-(2-imidazolin-2-yl) propane dihydrochloride], 1.5 ml of a 1 g/l solution of sodium hypophosphite, 2.25 ml of a solution containing 1 g/l of tert-butyl hydroperoxide, 3.0 ml of a 1 g/l solution of ammonium sulfate and iron (II) hexahydrate (Mohr salt).

After a few minutes the nitrogen inlet is closed and the reactor is closed. The polymerization reaction takes place for 2 to 5 hours until a peak temperature is reached. The rubbery gel obtained is chopped into particles with a size of between 1 and 6 mm.

500.0 g of previously minced gel are then mixed with 18.0 g of 50% sodium hydroxide solution, the mixture is heated and maintained at a temperature of 90° C. for a duration of 90 minutes.

The gel is then dried and milled to obtain the polymer in powder form.

Example 20 Preparation of Post Hydrolyzed P'3 Copolymer of acrylamide/2-acrylamido-2-methylpropanesulfonic acid that is not the Hydrated Crystalline Form (75/25 mole %)

The copolymer is prepared as in Example 19, replacing the 2-acrylamido-2-methylpropanesulfonic acid of hydrated crystalline form (Example 2) with 2-acrylamido-2-methylpropanesulfonic acid synthesized in example 1 that is not the hydrated crystalline form.

The invention claimed is:

1. A hydrated crystalline form of 2-acrylamido-2-methylpropane sulfonic acid having a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, and 46.04° degrees, all peak values being +/−0.1°.

2. A hydrated crystalline form of 2-acrylamido-2-methylpropane sulfonic acid according to claim 1, wherein it presents a Fourier transform infrared spectrum comprising peaks at 3280 $cm^{-1}$, 3126 $cm^{-1}$, 1657 $cm^{-1}$, 1595 $cm^{-1}$, 1453 $cm^{-1}$, 1395 $cm^{-1}$, 1307 $cm^{-1}$, 1205 $cm^{-1}$, 1164 $cm^{-1}$, 1113 $cm^{-1}$, 1041 $cm^{-1}$, 968 $cm^{-1}$, 885 $cm^{-1}$, 815 $cm^{-1}$, and 794 $cm^{-1}$, all peak values being +/−8 $cm^{-1}$.

3. The hydrated crystalline form of 2-acrylamido-2-methylpropane sulfonic acid according to claim 1, wherein it presents minimum ignition energy greater than 400 mJ.

4. The hydrated crystalline form of 2-acrylamido-2-methylpropane sulfonic acid according to claim 1, wherein it presents 4 thermal phenomena with the Differential Scanning calorimetry technique at 70° C., 100° C., 150° C. and 190° C., all +/−10° C.

5. The hydrated crystalline form of 2-acrylamido-2-methylpropane sulfonic acid according to claim 1, wherein it has a water/2-acrylamido-2-methylpropane sulfonic acid molar ratio of 1:1.

6. The hydrated crystalline form of 2-acrylamido-2-methylpropane sulfonic acid according to claim 3, that presents minimum ignition energy greater than 500 mJ.

\* \* \* \* \*